US006977175B1

(12) United States Patent
Horvitz et al.

(10) Patent No.: US 6,977,175 B1
(45) Date of Patent: Dec. 20, 2005

(54) **NUCLEIC ACIDS ENCODING *LIN-37* AND USES THEREOF**

(75) Inventors: H. Robert Horvitz, Aurburndale, MA (US); Xiaowei Lu, Arlington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/087,136

(22) Filed: May 28, 1998

Related U.S. Application Data

(60) Provisional application No. 60/047,996, filed on May 28, 1997.

(51) Int. Cl.[7] .......................... C12N 15/63; C12N 1/15; C12N 1/21; C12N 5/10; C07H 21/04
(52) U.S. Cl. .............................. 435/320.1; 435/252.3; 435/254.11; 435/325; 536/23.5
(58) Field of Search .............................. 536/23.1, 23.5; 435/320, 320.1, 252.3, 254.11, 325

(56) References Cited

OTHER PUBLICATIONS

Maruyama, Gene 120:135, 1992.*
Gene Bank Accession No. U00047, May 10, 1994.*
Basic Methods in Molecular Biology, Davis et al Editor 1986 Elsevier Science Pubishing Co, pp. 296-297.*
Burgess et al (Journal of Cell Biology, 1990, vol. 111, pp. 2129-2138).*
Lazar et al, 1988, Molecular and Cellular Biology vol. 8, pp. 1247-1252).*
Verma et al, Nature, 1997, vol. 389, pp. 239-242.*
Eck et al, Gene-Based Therapy, In: The Pharmacological Basis of Therapeutics, Goodman and Gilman, Ed.s, 1996, pp. 77-101.*
Orkin et al, "Report and Recommendation of the Panel to Assess the NIH Investment in Research on Gene Therapy", NIH, 1995.*
E.M. Hedgecock and R.K. Herman "The ncl-1 gene and genetic mosaics of *Caenorhabditis elegans*" Genetics 141: 989-1006 (1995).
E.L. Ferguson and H.R. Horvitz "The Multivulva Phenotype of Certain *Caenorhabditis elegans* Mutants Results from Defects in Two Functionally Redundant Pathways" Genetics 123:109-121 (1989).
H. R. Horvitz et al., "Isolation and Genetic Characterization of Cell-Lineage Mutants of the Nematode *Caenorhabditis elegans,*" Genetics 96:435-454 (1980).
T. Hunter, "Oncoprotein Networks," Cell 88:333-346 (1997).
C. J. Ceol and H. R. Horvitz, "*lin-55* DP and a *C. elegans* E2F-like gene act in a pathway with *lin-35* Rb to negatively regulate vulval induction," p. 65, meeting abstract booklet, 1998 East Coast *C. elegans* Meeting, Jun. 5-7, 1998, Boston, Massachusetts.
C. J. Ceol and H. R. Horvitz, "Identifying interactions of the synthetic multivulva genes," p. 65, meeting abstract booklet, 1996 East Coast *C. elegans* Meeting, Jun. 9-11, 1996, New Brunswick, New Jersey.
C. J. Ceol and H. R. Horvitz, "Cloning and characterization of the synthetic multivulva class B genes *lin-52* and *lin-55*," p. 622, meeting abstract booklet, 11th International *C. elegans* Meeting, May 28-Jun. 1, 1997, Madison, Wisconsin.
X. Lu and H. R. Horvitz, "Molecular analysis of the class B synthetic multivulva gene *lin-37*," p. 64, meeting abstract booklet, 1996 East Coast *C. elegans* Meeting, Jun. 9-11, 1996, New Brunswick, New Jersey.
X. Lu and H. R. Horvitz, "Molecular analyses of the class B synthetic multivulva gene *lin-37, lin-35*, and *lin-53,*" p. 389, meeting abstract booklet, 11th International *C. elegans* Meeting, May 28-Jun. 1, 1997, Madison, Wisconsin.
X. Lu and H. R. Horvitz, "The class B synthetic multivulva genes act in a Rb-mediated pathway to antagonize ras signaling," p. 38, meeting abstract booklet, 1998 East Coast *C. elegans* Meeting, Jun. 5-7, 1998, Boston, Massachusetts.
J. Thomas and H. R. Horvitz, "The synthetic multivulva genes may encode components of a cell signalling system," p. 515, meeting abstract booklet, 11th International *C. elegans* Meeting, Jun. 3-7, 1995, Madison, Wisconsin.

* cited by examiner

Primary Examiner—Karen A. Canella
(74) Attorney, Agent, or Firm—Kristina Bieker-Brady; Clark & Elbing LLP

(57) ABSTRACT

The invention provides novel genes involved in cell fate and cell proliferation, including lin-37, lin-35, lin-53, lin-55, lin-52, and lin-54 in multiple species and an E2F-1 gene of *C. elegans*. Methods for utilizing the genes and encoded proteins are also provided.

35 Claims, 22 Drawing Sheets

>lin-37 protein sequence
MSEIDPLAEFLLPEDGDRNARQNDPLISGGPLPLESPSRKLTSLLSYDPTVPESPDMK
FARKRLGNLLTTIKHHPSEIIGVLPEDYTRADEEPGRQGRPPGRPRKMPRHESSTSLM
ESPRKTMTRDSKIMFELRGKPFEMIAGRFEEEYSLGRAWVKGHMNNEYEPIKAQRTD
YAPNLAVDYLACREIHRMPRPDKSIPELPIVPSRIDEFDATVDPRYETDLKNEYIRH
WKQVKKGWCAHQRRRTAPHARSIALINKIYQPGESKTVEQALGLI

SEQ ID NO:1

FIG. 2

>lin-37 cDNA sequence
ATGTCAGAAATAGATCCACTTGCCGAGTTCTTGCTTCCAGAAGACGGAGATCGAA
ATGCTCGTCAAAATGATCCATTGATAAGCGGAGGTCCACTTCCATTGGAATCGCCA
AGCAGAAAACTCACATCCCTGTTATCCTATGATCCGACAGTTCCGGAGTCACCGGA
TATGAAATTCGCCAGAAAACGTCTGGGAAATCTGCTGACAACCATAAAACATCA
CCCATCGGAAATAATTGGAGTACTCCCAGAAGATTATACTCGTGCTGATGAAGAG
CCCGGGCGCCAAGGACGTCCACCAGGTCGCCCTCGTAAGATGCCGCGTCACGAATCTT
CAACTTCACTTATGGAATCACCACGCAAGACTATGACTCGTGATTCTAAAATTAT
GTTTGAATTGCGTGGAAAACCATTCGAAATGATAGCTGGACGTTTTGAAGAAGA
ATATTCACTTGGTAGAGCATGGGTTAAAGGACACATGAATAATGAATATGAACC
AATAAAAGCTCAAAGGACAGACTATGCACCGAATCTGGCTGTTGATTATCTTGCA
TGTCGCGAGATTCATCGAATGCCACGTCCAGATAAATCAATTCCTGAGCTGCCAAT
TGTTCCATCTAGAATCGATGAATTCGACGCTACAGTCGATCCAAGATATGAAACA
GATTTGAAAAATGAATACATTCGTCATTGGAAACAAGTCAAAAAAGGTTGGTG
TGCTCATCAACGTCGTCGGACTGCTCCCCATGCAAGAAGCATAGCATTAATCAACA
AAATCTACCAGCCTGGAGAGTCGAAAACTGTCGAGCAAGCACTTGGTCTTATTTA
AATATTCTAACATGTAATTTCAATTTATCTCTTACTTTCTGATCTTGCTATCACA
TGTCTCTTATTTCAAAAATCTCACTTTAAAATTCATATAAATAATGGGTTTATT
CAAATACATCATCTTGAC

SEQ ID NO:2

FIG. 3

>LIN-35 protein sequence
MPKRAADEPGTSTTDPFHEQSPFDAVLAGTETTDTICEEPPAKRIDLDIKQEFNGGVQ
SGGLIKNESELTQMTTKQETEGNINEARREEEDEEQDEDSRTSMPPALGEDDDYEEDDA
DSFIDKTNTPPPSQSFLEGCRAANLPNDIVTGAWETYNHAVQRVSLEGSESAWQLS
AIYYYLLSKGIKRRGKTIRILIQPFPVSILTIANSFDISVAEMLDKTARFVEIIHSRKIR
RYQEYIRRIQEGLAVSCVIFKKFCRIFCKIFEEIKVGSENCPSSHELFTVLWTSFLVMK
SRMTVDDLISNYQLLFSILDQVYTEMCSMKEGIVHHLNQKFVEDLLENDCTIIRALCT
QFGGSVLDARHFSDHTFKKMEKTGIPSTWNFQEFRDLIMNVPKTAYENYLLQRGSID
ERIFIPSVEDFSKIFQSPDTYSVADILKVSYSGRRFRDAEFLTKISNNHCLEKLALGGK
VASEKLVTQSKEQPRVPCVEYNLELGNYPDDLESNNQSLYNRLTKIIGSWKLENSKLE
EVCGTMSDSPMATILLKSDEMTNKFERTLSAELGETINENIPKYHYNVRKELELVFLI
FMEKIIVAELKKKVREEDLLNVIRREEFLDSVFCFCVELILVSNGYDRPFPWSAELCG
VHPFMFHKVIDLMITHEKQLSRQMVQHFSRIEETVIEYFSWKSDSPLWPMVVRCPF
AHFQEFGEDWADKLNSYSPIKFTPIKKPDDLRDELGRPIVPQNQTSRTLRIFLKRTYFT
AARRLQDLTDRVSMGARAKSQCWSLFDYLLRNDTLIFMDRHLDQILLCCVFVIMKI
NESSMLFTEIMAQYRRQSANSLLVYRSVTVFQEQLNPENPQAVNTKETILERLEGPQ
KEKTTVDIIKYYNIEFRDRIKYIIGQIDSASDEDLMEMPVATESGLMPVRVYLTHKLS
IQTLPKTKHGESKQERAIANLEKSGITIAMERSGD SEQ ID NO:3

FIG. 4

>lin-35 cDNA sequence
CCAAGTTTGAGACTGGTAAAAACTTCTTCAATATGCCGAAACGAGCAGCCGATGA
GCCTGGAACATCAACAACTGACCCATTTCACGAGCAAAGCCCATTCGATGCCGTGT
TAGCCGGCACGGAGACAACGGATACAATATGTGAAGAGCCACCAGCAAAACGAA
TCGACTTAGATATAAAGCAAGAATTCAATGGTGGAGTGCAAAGTGGAGGGCTGA
TTAAAAATGAATCCGAATTGACTCAAATGACAATCAAACAAGAAACAGAAGG
AAACATAAATGAAGCTAGACGAGAAGAAGAAGACGAAGAACAAGATGAAGA
TTCCAGAACATCAATGCCACCTGCATTGGGAGAAGATGATGATTATGAGGAGGAT
GATGCTGATAGTTTTATTGATAAAACTAATACACCGCCACCATCACAATCATTTC
TGGAAGGATGTCGAGCAGCTAATTTACCAAATGACATTGTTACTGGTGCATGGGA
AACGTACAACCACGCGGTTCAACGGGTTTCTCTTGAGGGTTCGGAATCGGCGTGGCA
ACTATCAGCAATTTACTATTATCTTCTATCAAAAGGAATAAAACGTCGTGGAAA
AACAATCCGTATTCTCATTCAACCGTTTCCTGTTTCGATACTTACAATTGCCAACT
CATTTGACATATCCGTTGCTGAAATGCTTGACAAAACTGCTCGATTTGTGGAAAT
TATACATTCCAGAAAAATTCGTCGTTATCAAGAATATATTCGACGAATTCAAGA
AGGACTCGCAGTTTCTTGTGTGATATTCAAAAAGTTTTGCCGAATTTTCTGCAAA
ATATTCGAGGAGATCAAAGTTGGATCCGAAAATTGTCCATCTTCTCATGAACTTT
TTACGGTTCTTTGGACATCTTTTCTGGTGATGAAAAGTCGAATGACAGTGGACGAT
TTGATTTCAAATTATCAACTTCTTTTTTCAATACTTGATCAAGTATATACCGAA
ATGTGTTCAATGAAAGAGGGAATAGTTCATCATTTGAATCAAAAATTTGTTGA
AGATCTTCTTGAAAATGATTGTACGATTATTCGAGCTCTTTGCACACAATTTGGT
GGAAGTGTTCTTGATGCACGGCACTTTTCTGATCATACTTTTAAGAAAATGGAGA
AGACTGGAATTCCGTCCACTTGGAATTTTCAAGAGTTTCGAGATTTGATCATGAA
CGTTCCAAAAACGGCATATGAGAATTATCTATTGCAACGTGGAAGTATTGATGA
GCGGATTTTCATTCCAAGCGTTGAGGACTTTTCAAAAATTTTCCAATCCCCGGACA
CATACTCAGTAGCAGATATTCTCAAAGTGTCTTACTCTGGAAGACGTTTCCGTGAT
GCAGAATTTCTTACAAAAATCTCAAATAATCATTGTCTGGAAAAGTTGGCATTA
GGTGGAAAAGTAGCATCAGAAAAGTTGGTAACACAGTCAAAAGAACAGCCGAG
AGTTCCGTGTGTTGAGTATAATCTCGAATTGGGAAATTATCCAGACGATTTGGAA
TCGAACAATCAAAGTCTTTATAATAGATTGACAAAAATTATTGGAAGCTGGAA
ATTGGAGAATTCGAAACTCGAAGAAGTGTGTGGCACAATGTCCGACAGTCCAATG
GCAACAATTCTTCTGAAAAGTGATGAAATGACAAATAAATTCGAGCGAACTTT
ATCTGCAGAACTCGGAGAGACGATCAATGAGAATATTCCTAAATATCACTATAA
TGTTCGAAAAGAATTGGAATTAGTTTTTCTCATTTTCATGGAGAAAATAATTGT
TGCAGAATTGAAAAAGAAAGTACGAGAGGAGGACTTGCTGAATGTGATTCGTCG
GGAAGAATTTCTTGATTCAGTTTTCTGTTTCTGTGTTGAACTGATCCTTGTTTCCA
ATGGATATGATCGTCCATTTCCATGGAGTGCTGAACTGTGTGGAGTACATCCATTT
ATGTTTCATAAAGTAATTGATTTGATGATAACACATGAGAAACAGCTAAGTCGT
CAAATGGTTCAACATTTTAGTCGAATTGAAGAAACTGTAATTGAGTATTTTTCG
TGGAAGTCTGATAGTCCATTATGGCCAATGGTTGTCAGGTGTCCATTTGCACATTT
TCAAGAATTCGGAGAGGATTGGGCTGATAAATTAAACTCGTACTCACCAATAAA
ATTCACTCCAATCAAGAAGCCTGATGATCTACGAGACGAACTTGGAAGACCTATA
GTTCCTCAAAATCAAACTTCAAGAACTCTAAGAATTTTTTTGAAAAGAACTTAT

FIG. 5 PAGE 1 OF 2

```
TTCACCGCCGCTCGTCGACTTCAAGATCTCACTGATCGTGTTTCAATGGGAGCTCGTG
CAAAATCACAATGCTGGTCACTTTTCGATTATCTTCTTCGCAATGACACTTTGATT
TTTATGGATAGACATCTTGATCAAATTCTTCTTTGTTGCGTGTTTGTCATTATGAA
GATAAATGAGTCATCAATGCTTTTCACGGAAATAATGGCTCAATATCGACGACA
ATCAGCCAATTCTTTGCTGGTCTACCGAAGTGTTACAGTATTCCAAGAACAACTG
AATCCCGAAAATCCACAGGCAGTAAACACGAAGGAGACAATTTTGGAACGTCTT
GAAGGTCCACAAAAAGAAAAAACGACAGTTGATATAATCAAATATTATAATA
TCGAGTTTCGGGATCGTATCAAGTATATTATCGGTCAAATTGATAGTGCTTCAGA
TGAAGATTTGATGGAAATGCCGGTTGCAACAGAATCTGGATTGATGCCTGTTCGA
GTTTATTTAACACATAAATTATCGATTCAAACGCTTCCAAAAACGAAACACGGA
GAGTCGAAACAAGAAAGAGCTATTGCGAACCTTGAAAAATCTGGAATTACGATC
GCTATGGAACGGTCTGGAGATTAAAAATGATTGTTGTGAATACTTTGAACTTTTT
AATGCATTTTTGATTAATCATTTAGTACTTCTTTTCTCGTCTATTTTTTTATCTTT
TCCTTCAAATTCAGGCAAGTAATTATACTTTCCATTTCTAATTGATTGCTTCAAA
ATAGACGTCTAGTTATATTCAAAACAATCCCCCTTTTGAATTGGAATCTTCAAAT
ATCGTATTAAATATTAATATTGTAATCATTTTTCACAATCCCCCATGCCATTATT
GTTACTGATTTTTTCTCTCTTTTTAACCATCATCGATAAATTCATTTTACAGTTAT
AAAAAAAAAAAAAAA        SEQ ID NO:4
```

FIG. 5    PAGE 2 OF 2

>LIN-53 protein
MATLEDGTSEDRVANDEYKIWKKNTPFLYDLVMTHALEWPSLSVQWLPDVAKDN
SDHTIHRLILGTHTSDEQNHLLISKICMPTDDAQFDASRYDTERSEYGGFGAVNGKVE
PDIRINHEGEVNRARYMPQKSNIIATKSPHADVYIFDYLKHSAVPRDNTFNPLIRLK
GHTKEGYGLSWNPNKEGLILSASDDQTVCHWDINANQNVAGELQAKDVFKGHESV
VEDVAWHVLHDGVFGSVGDDKKLLIWDVRTSTPGHCIDAHSAEVNCLAFNPYSEFI
LATGSADKTVALWDLRNLRMKLHSFESHRDEIFQVQWSPHNETILASSGTDKRLHV
WDLSKIGEDQSAEDAEDGPPELLFIHGGHTAKISDFSWNPNEPWVVCSVSEDNILQV
WQMADNIYNEVDEETPADVVERQQ    SEQ ID NO:5

FIG. 6

>lin-53 cDNA
GAAATGGCCACTCTTGAAGATGGAACCTCCGAAGATCGCGTCGCAAATGATGAAT
ACAAAATTTGGAAAAAGAACACCCCGTTCTTGTACGATCTCGTAATGACACATGC
GCTTGAGTGGCCTTCACTCAGTGTTCAATGGCTCCCAGACGTTGCGAAGGATAACAG
CGACCATACTATTCATCGGCTCATTCTTGGAACTCATACTTCAGATGAGCAGAATC
ACTTGCTTATTTCTAAGATCTGTATGCCAACGGATGATGCCCAATTTGATGCATCT
CGCTACGATACCGAGCGCAGTGAATACGGTGGTTTCGGAGCTGTTAACGGAAAAGT
GGAACCCGATATTCGCATTAACCACGAAGGGGAGGTTAACAGAGCTCGTTACATG
CCTCAAAAGTCGAATATCATTGCTACAAAGTCTCCACATGCTGATGTTTACATTT
TCGACTATTTAAAGCACTCTGCTGTTCCTCGTGATAACACGTTCAATCCGCTTATCA
GACTGAAAGGACACACGAAGGAAGGCTATGGATTATCATGGAATCCAAACAAA
GAAGGTTTGATTCTATCAGCGTCAGATGATCAGACAGTTTGTCATTGGGATATCA
ACGCAAATCAGAATGTTGCCGGGGAATTGCAAGCGAAGGATGTTTTCAAAGGTCA
CGAGTCAGTCGTTGAAGATGTTGCTTGGCACGTTTTGCATGATGGTGTCTTCGGATC
GGTTGGTGACGATAAGAAATTGCTCATTTGGGATGTGCGCACAAGCACTCCTGGAC
ACTGTATCGATGCTCATTCTGCCGAAGTTAACTGTCTCGCATTCAATCCATATTCCG
AATTCATTCTGGCCACCGGATCAGCTGATAAAACTGTCGCTCTTTGGGATCTACGT
AATCTACGAATGAAACTTCACTCATTTGAATCACATCGTGATGAAATCTTCCAAG
TTCAGTGGAGTCCACACAACGAGACTATTCTTGCATCCAGCGGTACTGATAAACGT
CTTCATGTGTGGGACCTATCTAAGATTGGAGAAGACCAATCTGCCGAAGACGCGGA
AGATGGTCCACCAGAGCTGTTGTTTATTCACGGTGGGCACACCGCCAAGATCAGCG
ATTTCTCGTGGAACCCGAACGAGCCTTGGGTTGTGTGCAGTGTGTCAGAAGACAAT
ATTCTCCAAGTGTGGCAAATGGCTGATAACATATACAACGAAGTTGACGAAGAA
ACTCCAGCCGATGTGGTAGAGAGACAACAGTAAAATACGTGAAACGCGCTTAAA
TTATTTGTATTTAACTTCTATCCTTCTTTAATTTTGCATCTCAACAAATTGTTCAT
CTTACCATTTATTCAAACGCATATTCTTCACCAACTAAGTTTTTAAAGTTAAAA
TGTTACCTTGAGATATGATCATATTTTGTTGAACCTGAAATAAATTCGATGACCA
TTGTCAAAAAAAAAAAAAAAAA    SEQ ID NO:6

FIG. 7

PARTIAL lin-55 TRANSCRIPT WITH PREDICTED TRANSLATION

FIG. 8

Notes: The 3' untranslated region has not been sequenced.

*C.elegans* E2F-1 Protein Sequence

1
MELQKALEMTKQSSIKNNLMLGLDNELDFDFDFDEDEDLDQPQMGTR
ADKSLGLLAKRFIRMIQYSPYGRCDLNTAAEALNVRQKRRIYDITNVLE
GIGLIEKRSKNMIQWKGGDFMLNVKEGKRLSATTEEEDRMEQLKAEIE
QLNKEEELIEQRQRWLQQSLRNMTESVENNKLSYVLRSQLAEIQGSDLT
IGIQTRVGTQVRLSDPEQVEIHGGPSWCYLKDPSGPLRAAIVSNHELHDF
VQRERAKRPGEEHVDADAPDEMMDDSRYRNRRTINDDEMFGFEQKVP
AMKHLEPPPASDDYVYSSTGDEYRGDSIVDLYGD
　　　　　　　　　　　　　　　　　324

SEQ ID NO:9

FIG. 9

*C.elegans* E2F-1 cDNA Sequence

1
GTTTGAGCCATGGAAGACTCGTACAACGACATGGAAGACCCCGGC
TTCCGCCAATTATCTGACATGGAGCTTCAAAAAGCGCTGGAAATGA
CCAAACAGAGCTCGATAAAGAACAATTTGATGCTCGGGCTCGACA
ATGAGCTTGACTTTGATTTTGATTTTGACGAGGATGAGGACCTGGAT
CAACCACAAATGGGCACACGAGCCGATAAATCGTTGGGATTGTTG
GCGAAACGATTTATTCGAATGATTCAGTACTCACCGTATGGAAGAT
GCGATTTGAACACTGCCGCCGAGGCGCTCAATGTCCGGCAAAAGC
GACGAATCTACGATATTACGAATGTTCTCGAAGGAATTGGTCTTATT
GAGAAAAGAAGCAAGAATATGATACAGTGGAAAGGCGGTGATTTT
ATGCTAAACGTGAAGGAAGGGAAACGACTATCGGCCACAACAGA
AGAAGAAGATCGAATGGAACAATTAAAAGCTGAAATTGAGCAATT
AAATAAGGAAGAAGAGCTCATTGAGCAACGTCAAAGATGGCTTCA
GCAGAGCCTCCGAAACATGACAGAATCCGTGGAGAACAACAAGCT
CAGCTATGTGCTCCGTTCACAGCTCGCCGAGATTCAAGGCTCAGAT
CTTACGATTGGAATTCAAACGAGAGTCGGCACACAAGTTCGGCTCA
GTGATCCGGAGCAAGTCGAGATACACGGTGGACCATCTTGGTGTTA
CCTGAAAGATCCCTCTGGACCCCTCCGAGCCGCCATCGTTTCCAAC
CATGAGCTACATGATTTTGTACAGAGAGAACGAGCAAAACGGCCT
GGTGAAGAGCACGTTGACGCTGATGCTCCAGATGAAATGATGGAT
GATTCAAGATATCGGAATCGGCGGACGATCAATGATGATGAAATG
TTTGGTTTTGAGCAGAAAGTCCCAGCGATGAAGCATCTGGAGCCAC
CACCGGCCAGCGATGACTACGTTTATTCGAGCACCGGAGACGAGT
ATCGAGGAGATTCTATAGTCGATTTGTACGGAGATTAATTATTTTAA
TATTTTTTTTTTAAATTTCGAATTCTGCGACCATTTCTCATTTGACATC
TATTCATTTACTCCAAATTCCAAATTTTTCCCCAAAAAAATTATCGA
TGTTTCGGCTCCAAATGTTATTATTTTCCCATCCACAGTGCCCACAC
AATTCATAATGTGCCTCTGGAGAAAACCTAACGTATTTCAATTTCTA
TCCCAAATTTTTATTTTTCAAAAATTTCTCAGATTTTTAAATTATTTG
TCACACTTTTTTCTGTATTCAAACTGAACTTTTTCACTTGGATTTGTA
CGTTTTTTTTTTGTTCAATTTTAATGGATTTTCACTTGAAAACCCCA
ATAAAAACGGGATAAATCGACGTTTTTGAATAAAAAAAAAAAAAA
AA     SEQ ID NO:10
1428

FIG. 10

LIN-52 Protein Sequence

1
MSRPLGFIGYEFGDDEMFVQQMIEKKSNAEQAKMLEQQKKMLECTET
MPEESEPVPMKCLDFEEAFQSESVSKGYESPYKNISFLKEDAVTVNTMSH
CPADDIAKLIRNIQNSVYTLGIEEARQCRRGKLLNVLKPTGSASPRYLQP
TPPKNVAEETTGSQ   SEQ ID NO:11
              161

FIG. 11 lin-52 cDNA Sequence

1
ATGTCGCGTCCGCTAGGATTTATTGGATACGAATTTGGAGATGACG
AAATGTTCGTCCAACAAATGATCGAAAAGAAATCAAACGCAGAAC
AGGCGAAAATGCTTGAACAACAGAAAAAGATGCTCGAATGCACCG
AAACAATGCCAGAAGAAAGTGAGCCAGTTCCAATGAAATGTCTCG
ATTTTGAAGAAGCATTTCAAAGCGAATCAGTATCAAAAGGTTACGA
ATCGCCATACAAGAATATTTCGTTTCTCAAGGAAGATGCTGTGACT
GTTAATACAATGAGCCACTGCCCAGCCGACGATATCGCCAAGCTCA
TCCGAAACATTCAAAACTCGGTGTACACTCTTGGAATCGAAGAAGC
TCGCCAGTGCCGACGTGGAAAGTTGCTCAACGTGCTGAAACCCACT
GGCTCGGCTTCTCCGAGATATTTGCAGCCAACACCACCGAAAAATG
TAGCGGAAGAAACGACAGGAAGCCAGTGAAATTGAA   SEQ ID NO:12
                                   493

FIG. 12 lin-54 Protein Sequence

1
MNQGEIVYQDDDDYYDESEIYDNYEEGAEFIEVNGQLVPHNPNLQAQ
QNRPGTSSMIQQHNRSMEVNQGLVKDEPIDTSSHRVYVPPPRPVQRKL
WKLFQPGPSTPGSSQYTVRNLSNLSGSPSMYDRQPASLPRTVQPMGLEM
GNSEQRKVYIDMKDHVSHIRLKTKKKVFAPGQRKFCNCTKSQCLKLYC
DCFANGEFCRDCNCKDCHNNIEYDSQRSKAIRQSLERNPNAFKPKIGIA
RGGITDIERLHQKGCHCKKSGCLKNYCECYEAKVPCTDRCKCKGCQNT
ETYRMTRYKNSGGAVSNTNALMSLTNASSTATPDSGPGSVVTDEHGDD
YEDMLLSHKPKVEMDPRRFPWYYMTDEVVEAATMCMVAQAEEALNY
EKVQTEDEKLINMEKLVLREFGRCLEQMITNITELTQDLDAAPTDDIPG
PSTSTS
438
SEQ ID NO:13

FIG. 13 lin-54 cDNA Sequence

1
ATTTTCAGTGTTGACAATCAATCAAGGAGAAATCGTTTATCAAGAC
GACGATGATTATTACGACGAATCGGAGATATACGATAATTATGAAG
AAGGTGCCGAATTTATCGAAGTTAATGGACAGCTTGTGCCTCATAA
TCCAAACTTACAGGCGCAGCAAAATCGTCCGGGAACCTCGAGTAT
GATTCAACAGCATAATCGATCAATGGAAGTTAATCAGGGATTGGTC
AAAGACGAACCAATTGATACATCATCGCATCGCGTCTACGTCCCCC
CTCCGAGACCAGTTCAGCGAAAACTTTGGAAGCTTTTTCAGCCTGG
GCCCAGCACTCCCGGATCGTCTCAGTACACTGTGCGGAATTTGTCC
AATTTATCGGGTTCACCTTCAATGTACGATCGACAGCCCGCTTCATT
ACCTAGAACAGTGCAACCAATGGGCTTGGAGATGGGAAATTCTGA
ACAGCGAAAAGTTTACATCGATATGAAAGATCACGTTAGTCATATT
AGATTGAAAACTAAAAAAAAAGTATTTGCACCTGGCCAGCGGAAA
CCATGCAATTGCACGAAATCTCAATGCCTCAAGCTCTACTGTGATT
GTTTCGCCAATGGAGAGTTCTGTCGTGACTGCAATTGCAAGGATTGT
CACAATAATATAGAATACGACAGTCAGCGTTCAAAAGCCATCCGT
CAGTCACTTGAGCGAAATCCGAACGCTTTCAAGCCAAAAATTGGTA
TTGCTCGTGGAGGTATTACCGACATCGAACGTCTTCATCAGAAAGG
ATGTCACTGTAAAAAGAGTGGTTGTCTGAAAAACTATTGTGAGTGT
TATGAAGCAAAGGTTCCGTGTACCGATCGATGCAAGTGCAAAGGA
TGTCAGAATACTGAAACATACAGAATGACAAGATACAAGAACTCC
GGTGGTGCCGTGTCCAATACGAATGCCCTGATGTCATTCACCAACG
CTTCCAGCACAGCGACTCCAGATTCTGGTCCGGGAAGTGTGGTGAC
CGATGAGCATGGAGACGACTACGAGGATATGCTTCTTTCGCATAAA
CCGAAGGTCGAGATGGATCCTAGACGCTTCCCGTGGTACTATATGA
CCGATGAAGTCGTTGAGGCAGCCACTATGTGCATGGTTGCTCAAGC
TGAACAAGCTTTAAACTACGAAAAAGTGCAAACCGAAGACGAAA
AACTCATCAATATGGAGAAGCTTGTCCTTCGTGAATTCGGCCGCTGT
CTCGAACAAATGATCACAAACACAACTGAGCTCACACAAGATCTT
GATGCCGCTCCAACGGATGACATCCCAGGACCATCTACTAGTACTT
CTTAACTATTCGCATTAAAATTATTATCAATTTTATCACAGTTGCGC
GATCTTTTATGATCTCACCTCTCACACATTCTTTGCCTTCCTCCCCTC
CTCTCAATGCTTTTACAGATTCACAAGTTGCCTTCTTTCAAAGTTGTC
AAATAAAAAATGATCAGAAAAATTTGTTTCAT
1503
SEQ ID NO:14

FIG. 14 lin-52

*lin-52* maps on LGIII between *unc-16* and *unc-69*.

lin-55

*lin-55* maps on LGII between *rol-6* and *unc-4*.

*lin-37* message is present in both embryonic and mixed-staged RNAs

Results indicate that LIN-36 is able to self-associate. No other interactions among the synMuvs were detected.

|  | | PREYS | | | |
|---|---|---|---|---|---|
|  | | lin-9 | lin-15A | lin-15B | lin-36 |
| BAITS | SNF1 (- control) | - | - | - | - |
|  | lin-9 | - | - | - | - |
|  | lin-15A | - | - | - | - |
|  | lin-15B | - | - | - | - |
|  | lin-36 | - | - | - | ++ |

Characterization of Molecular Interactions of the synMuv Gene Products

Future Search for Additional synMuv Alleles

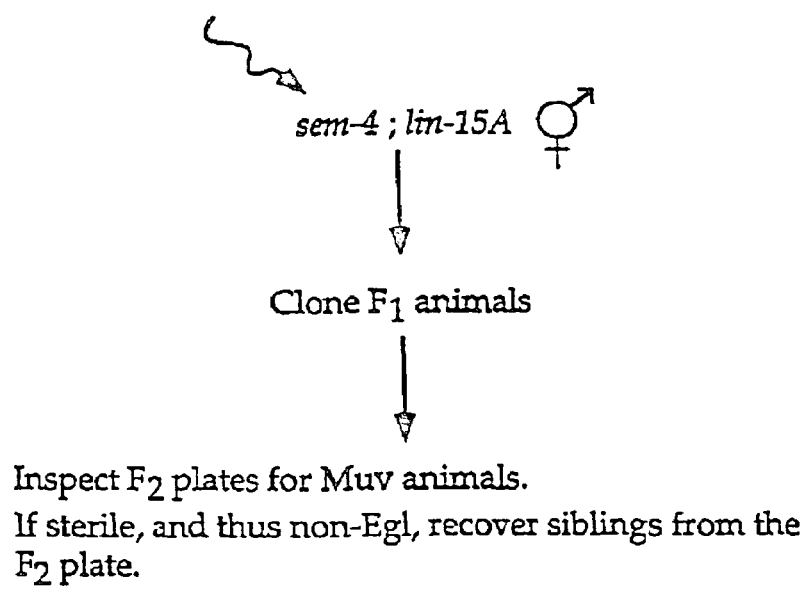

Inspect F₂ plates for Muv animals.
If sterile, and thus non-Egl, recover siblings from the F₂ plate.

FIG. 25

Sequence of *Mus musculus* cDNA clone vp19d01

```
1
GTGCTAAAACAATTGGTGAACCAGACTTGCCCAAAGTTGTTAATAT
TAACTTCTGTCCATCTGGTTTAAGGGTCTGATTGCCAAGTTTAAGAT
CAGATGTCTGTGATACTTTGTTTAAAATAATCTGATTGGCTGATATA
GTCACAGGAGTCTGAGCACCAAGTTTTTGAAGGCCACTTGGAAATG
CTGGTTTCACTGTGGTATTAGAATCTGCTTTAGAAACTGTGGTATTC
ACTGCAACTTGGTTAGTGTGGTTACTGTACACTGTGATTGGTTCCGT
GGAAATGGGCGTGGCTGTAGAGTCACCGGTAGAATTTATGTTGACA
ATTTCTTCCAGCTCTGTCTCCATGGGAATTGGGGATGACACAATTAC
AGCCTCAATACTATCCTCATCCACTAACGTTATAGCAGTGTCCATTA
TGTCGTCTGGAAGCAAACTATTCACTCGG
                                              449    SEQ ID NO:15
```

FIG. 26

*Homo sapiens* lin-54-like cDNA Sequence

```
1
AAACTGGTCCAAGCTGAATTCCGGGGAAAAGGTGAAAATGGCGGA
TCTTTCGAAATACAATCCCGGCCCCTGACATACCAGAGGCGGCGGC
GACGGCGACGTCGCCAACCCGGCTCCCTTCTCGGTCCCCGGGTACC
CTGGAGCGCTCCAGTTTGGACAAACTGGGAAAGGAAGCTGCTGGC
CAGAGCTATCGTGCACGGGCAAAACAAGCCCCGCCGGGGCTCGGG
ATTGCCCAGGACCTTCCGGAGCCCTACCTCGGAGCCCGAGGGAG
GAGAAAGCGGCAGCCGCTGGAGTGCCTGATCAACTTTCTAGCGGG
AGAACGATCATGGAGGTGGTGCCAGCTGAGGTGAATAGTTTGCTTC
CAGAGGAAATAATGGACACTGGTATAACTTTAGTGGATGATGATAG
TATTGAGGCTGTTATTGTTTCATCCCCAATTCCCATGGAGACAGAAC
TGGAAGAAATTGTCAACATAAATTCTACTGGTGACTCTACAGCCAC
GCCCATTTCCACGGAACCAATCACAGTGTACAGTAACCACACTAAC
CAAGTTGCAGTGAATACCACAATTACTAAAGCAGATTCTAATACCA
CAGTGAAACCAGCTTTTCCAAGTGGCCTTCAAAAACTTGGTGCTCA
GACTCCTGTGACTATATCAGCCAATCAGATTATTTTAAACAAAGTA
TCACAGACATCTGATCTTAAACTTGGCAATCAGACCCTTAAACCAG
ATGGACAGAAGTTAATTTTAACAACTTTGGGCAAGTCTGGTTCACC
AATTGTTTTAGCACTACCCCATAGCCAACTACCCCAGGCTCAGAAA
GTTACAACTCAGGCCCAGTCAGGAGATGCTAAGTTACCACCGCAGC
AAATTAAAGTAGTTACCATTGGAGGGAGGCCAGAGGTGAAACCTG
TCATTGGTGTCTCAGCATTGACCCCAGGAAGTCAACTGATTAATAC
TACAACTCAGCCCTCTGTGTTACAGACCCAACAGTTAAAAACAGTA
CAGATTGCTAAGAAGCCTCGAACGCCAACCTCTGGTCCAGTAATCA
CGAAGCTGATCTTTGCAAAACCAATTAATAGTAAAGCAGTTACAGG
ACAGACAACTCAAGTTTCACCACCAGTCATTGCAGGTAGGGTTCTT
TCACAGTCTACTCCCGGAACTCCATCAAAGACCATAACAATATCTG
AAAGTGGTGTTATTGGATCAACTTTAAATTCTACAACACAGACACC
AAATAAAATAGCCATCTCACCTTTGAAATCGCCAAATAAGGCAGT
GAAATCAACTGTGCAGACCATCACTGTTGGAGGAGTGAGCACATC
ACAGTTTAAGACAATTATTCCTCTGGCAACTGCTCCCAATGTCCAG
CAGATTCAAGTGCCTGGAAGCAAGTTTCATTATGTCCGACTTGTTAC
TGCCACATCAGCCAGTAGCTCAACCCAGCCAGTTAGTCAGAATCCC
AGTACAAACACTCAGCCTTTTCAGCAAGCAAAGCCAGTGGTTGTTA
ATACAACCCCAGTGCGGATGTCAGTTCCAATTGTCTCAGCTCAGGC
TGTCAAACAAGTTGTTCCAAAACCAATCAATCCAACTTCACAAATA
GTAACTACTAGCCAGCCACAGCAACGGCTTATCATGCCTGCCACAC
CACTGCCACAGATCCAGCCCAACCTCACTAACCTGCCACCAGGCA
CTGTCCTGGCACCAGCTCCGGGAACAGGGAATGTGGGTTATGCAGT
GCTTCCAGCTCAGTATGTTACTCAGCTACAGCAGTCTTCATATGTAT
CAATAGCAAGCAACTCTACCTTTACTGGAACATCTGGTATCCAGAC
CCAGGCACGGCTTCCATTCAATGGCATAATCCCATCAGAGTCGGCC
AGTCGGCCCCGAAAGCCCTGTAATTGTACAAAATCACTGTGTTTGA
AATTGTATTGTGATTGCTTTGCAAATGGTGAATTTTGCAACAACTGC
AATTGTACTAATTGTTACAACAATTTG
                                                      2000
```

Homo sapiens lin-54-like cDNA Sequence, cont.

```
2001
GAACATGAAAATGAAAGGCAAAAAGCAATAAAGGCATGCCTTGA
CAGAAATCCAGAAGCCTTTAAGCCTAAGATAGGGAAAGGAAAGG
AGGGAGAATCTGATCGACGTCATAGCAAAGGGTGTAATTGCAAAC
GATCAGGATGTCTTAAAAACTACTGTGAATGCTATGAGGCAAAAAT
AATGTGTTCCTCAATATGCAAATGTATTGGCTGTAAGAATTTTGAAG
AAAGCCCGGAAAGGAAGACATTGATGCATTTGGCAGATGCAGCTG
AAGTAAGGGTACAGCAACAAACAGCAGCCAAGACGAAGTTATCCT
CTCAAATTTCAGACTTGCTTACTAGGCCAACACCAGCTTTAAATAGT
GGAGGCGGAAAATTGCCATTTACATTTGTAACTAAGGAANTANCTG
AAGCCACNTGTAATTGCCNCCTTGCCCAGGCAGAGCAGGCAGACA
AGAAGGGAAAATCAAAGGCAGCAGCGGAACGGATGATACTTGAG
GAATNCGGACNATGTTTGATGANTGTCATCAACTCTGCAGGAAAG
GCAAAAANTGACCCTTGTGCCCATGAATTGCTAACTCTTGCACAAA
AGACTGATAAATGGAACTGTACAGAAAATTTAAGGTGCAGGGACA
CTTGATTTTCTGGAAGAAAACAATTACTGTATTTTAATTCAGTCCT
TGTTTTAAAAGACCTGAAATTATAATACTGAAGGAGAAGAAATTTT
AAATGAGGAAATTAGTACATTTTAAATCTTAGTTAAATCTGCTTATG
CCCCTTCTAAATTGAATTTTTCTNTATTATATAGATTTTTTAATTTGC
TTGGGTTTCTTAAGAATTAGATGTTCTCTTTCTGATACCTTTGACAAA
AAATGTTTATAAATTCATATAATTTATAATGTATGGTGTTGTATGAC
TTTGTTAATAGAAAGCCAAAGCAGCAGTGGTTAGCACCCATTCTT
TGGGACTTGATCTAGAATATCTGCAGACAGAATGTTACATAAACAA
ATTCTTATGAAACACATTCAAATGACATTTTGTATTTAGAAAAGGA
CTATCTTTTAAAGAAAAAGCAGCCTTTTAGGGCCGATTCTGGAATA
ATATCCTGTTGTCACTTTGGGAATGTCAGAAGGGGAAACAATCCCC
AGGCACACTAAAAATTTTTTAAAGTTATTTAAAAAAACATATAAAA
TATTAAAGGACAGTAAATCTCAGAGGATGGGCAATGTGTTTCTATA
ATAAGGAAAGGCTAACAGATGCTCTGGGCTGTCTCCATTTTCTTTCA
AAGAGGTGGTATGTATTTGAAGTAATAAATTGTCAAAGTGATTACT
GGGTACTATTAAAATGATAGGTGGATATAAATGGAAGTAAACATTA
TGTAGTGATAATATAGAACCTCACATAGTAATCAAGTATAAAATTT
GGCATGGGTGGAGAAACAAAGNATCGGGAAGCTGCCAAAGATGA
ATTTAGAGAAGTTTTCATCTATACAATCAATTATTTTACAGACTTTT
TTTCCGGAATTCTTTTGCT
                3535    SEQ ID NO:16
```

NUCLEIC ACIDS ENCODING *LIN-37* AND USES THEREOF

CROSS REFERENCE TO RELATED APPLICATIONS

This application claims priority from U.S. provisional application Ser. No. 60/047,996, filed May 28, 1997.

BACKGROUND OF THE INVENTION

The field of the invention is cell proliferation.

Previously we have identified and studied the synthetic multivulva genes in the nematode *elegans. C. elegans* is well suited to developmental genetic studies because the entire cell lineage has been mapped and is essentially invariant from one animal to the next. Thus, by comparing the cell lineage of a wild-type animal to that of a mutant animal, the changes in cellular fates caused by the mutation can be determined.

A number of mutations that alter cell lineage, termed lin mutations, were obtained in genetic screens conducted by Horvitz and Sulston in the late 1970's. A subset of the mutations affected the formation of the vulva, a structure on the ventral surface of C. elegans hermaphrodites through which eggs are laid and through which sperm enters during cross-fertilization. Six vulval precursor cells have the potential to undertake a vulval cell lineage as defined by the number and pattern of cell divisions. In a wild type animal only three of these cells actually undertake vulval cell fates and these three cells generate the 22 cells that make up the adult vulva. In multivulva (Muv) animals, most or all of the six vulval precursor cells undertake vulval cell fates. In addition to the cells required for the formation of a normal vulva, these mutant animals generate an excess of cells which cause the formation of raised, vulva-like structures on the ventral surface of the animal. On the other hand, a vulvaless (Vul) phenotype results when no or too few vulval precursor cells adopt vulval cell fates.

Genetic and molecular analyses of Muv and Vul animals have defined a Ras signal transduction pathway that mediates induction of the hermaphrodite vulva. Mutant animals in which this pathway is ectopically activated can display a multivulva phenotype, whereas mutant animals that have reduced Ras pathway signalling can display a vulvaless phenotype. As in the worm, Ras pathways have been found to control cell proliferation in a range of organisms from the yeast *S. cerevisiae* to humans. Members of this pathway, most commonly Ras itself, have been shown to be mutated in a broad range of human cancers.

The synthetic multivulva (synMuv) genes act as negative regulators of worm signalling pathway. The first synthetic multivulva mutant was identified by Horvitz and Sulston. The two genetic loci mutated in this mutant were termed lin-8 and lin-9. Reduction-of-function mutations in both of these loci were required for a multivulva phenotype. Subsequent genetic screens identified a set of loci which fall into the same class as lin-8, termed class A genes, and genes which fall into the same class as lin-9, termed class B genes. In general, an animal with a reduction-of-function mutation in any class A gene and a reduction-of-function mutation in any class B gene will display a multivulva phenotype yet double mutant animals have wild type vulvae. Thus far four class A loci (lin-8, lin-15A, lin-38 and lin-56) and ten class B loci (lin-9, lin-15B, lin-35, lin-36, lin-37, lin-51, lin-52, lin-53, lin-54 and lin-55) have been identified genetically.

Molecular analyses of the synMuv genes have primarily dealt with the class B genes. lin-15A and lin-15B have been cloned and sequenced. Both genes encode novel protein with no known homologs in other species. lin-36 and lin-9 have also been cloned and encode novel proteins.

SUMMARY OF THE INVENTION

We have cloned synMuv genes in C. elegans that are part of a pathway which may be used as a genetic and biochemical model system for tumor suppression and, conversely, cancer. Specifically, we have now cloned lin-35, lin-37, lin 53, lin-52 and lin-54. The sequences of lin-35, lin-53, and lin-55 all have homology to proteins in the retinoblastoma tumor suppressor pathway family of proteins. This indicates that the synMuv pathway genes and proteins may be used to identify genes which are part of the mammalian pathway (e.g., by finding homologs of novel pathway genes such as lin-37, lin-52, or lin-54) and to identify genes, proteins, and therapeutic compounds which modulate this pathway.

The invention also features novel synMuv nucleic acids, proteins, and antibodies which bind these proteins.

In general, the invention features substantially pure nucleic acid (for example, genomic DNA, cDNA, or synthetic DNA) encoding a mammalian SynMuv polypeptide, as defined below. In related aspects, the invention also features a vector, a cell (e.g., a nematodes mammalian, yeast or bacterial cell), and a transgenic animal or embryo thereof which includes such a substantially pure DNA encoding a SynMuv polypeptide.

In preferred embodiments, lin-37, lin35, lin-53, lin-55, lin-52, lin-54, or the C.elegans E2F-1 is the gene. In most preferred embodiments the gene is a C. elegans/gene or a human or murine lin-54 gene. In other various preferred embodiments, the cell is a transformed cell. In related aspects, the invention features a animal containing a mutation in a gene which encodes a SynMuv polypeptide that is expressed in or delivered to a cell where a SynMuv gene is know to confer a phenotype.

In other aspects, the invention features a DNA sequence substantially identical to a DNA sequence shown in any one of FIG. 3, 5, 7, 8, 10, 12, 14, 26, or 27.

In another aspect, the invention also features RNA which is encoded by the DNA described herein. Preferably, the RNA is mRNA. In another embodiment the RNA is antisense RNA capable of decreasing at least one biological activity of a SynMuv gene.

In another aspect, the invention features a substantially pure polypeptide having a sequence comprising one of the SynMuv amino acid sequences shown in FIG. 2, 4, 6, 8, 9, 11, or 13 or encoded by a nucleic acid of FIG. 26 or 27.

In a second aspect, the invention features a substantially pure DNA which includes a promoter capable of expressing the SynMuv gene in a cell. In preferred embodiments, the SynMuv gene is lin-37, lin35, lin-53, lin-55, lin-52, lin-54, or C.elegans E2F-1.

In preferred embodiments, the promoter is the promoter native to a SynMuv gene. Additionally, transcriptional and translational regulatory regions are preferably native to a SynMuv gene.

The transgenic cells of the invention are preferably cells which are susceptible to cell death. In preferred embodiments the transgenic cell is a nematode, murine, or human cell.

In another aspect, the invention features a method of modulating cell death which involves producing a transgenic cell having a transgene encoding a SynMuv polypeptide wherein the transgene is integrated into the genome of the cell and is positioned for expression in the cell wherein the SynMuv transgene is expressed in the cell at a level sufficient to modulating cell death.

In another aspect, the invention features a method of detecting a SynMuv gene in a cell involving: (a) contacting the SynMuv gene or a portion thereof greater than 9 nucleic acids, preferably greater than 18 nucleic acids in length with a preparation of genomic DNA from the cell under hybridization conditions providing detection of DNA sequences having about 50% or greater nucleotide sequence identity to the amino acid encoding DNA sequences of lin-37, lin35, lin-53, lin-55, lin-52, lin-54, or C.elegans E2F-1.

In another aspect, the invention features a method of producing a SynMuv polypeptide which involves: (a) providing a cell transformed with DNA encoding a SynMuv polypeptide positioned for expression in the cell; (b) culturing the cell under conditions for expressing the DNA; and (c) isolating the SynMuv polypeptide. In preferred embodiments the SynMuv polypeptide is expressed by DNA which has a constituative or inducible promotor. In one embodiment, the promotor is a deterologous promotor.

In another aspect, the invention features substantially pure SynMuv polypeptide. Preferably, the polypeptide includes a greater than 50 amino acid sequence substantially identical to a greater than 50 amino acid sequence shown in any one of FIG. 2, 4, 6, 8, 9, 11, or 13 or encoded by a nucleic acid of FIG. 26 or 27. Most preferably, the polypeptide has at least one biological activity of a SynMuv protein of the immediately for going figures.

In another aspect, the invention features a SynMuv gene isolated according to the method involving: (a) providing a sample of DNA; (b) providing a pair of oligonucleotides having sequence homology to a conserved region of a SynMuv gene; (c) combining the pair of oligonucleotides with the cell DNA sample under conditions suitable for polymerase chain reaction-mediated DNA amplification; and (d) isolating the amplified SynMuv gene or fragment thereof.

In preferred embodiments, the amplification is carried out using a reverse-transcription polymerase chain reaction, for example, the RACE method.

In another aspect, the invention features a SynMuv gene isolated according to the method involving: (a) providing a preparation of DNA; (b) providing a detectably-labelled DNA sequence having homology to a conserved region of a SynMuv gene; (c) contacting the preparation of DNA with the detectably-labelled DNA sequence under hybridization conditions providing detection of genes having 50% or greater nucleotide sequence identity; and (d) identifying a SynMuv gene by its association with the detectable label.

In another aspect, the invention features a SynMuv gene isolated according to the method involving: (a) providing a cell sample; (b) introducing by transformation into the cell sample a candidate SynMuv gene; (c) expressing the candidate SynMuv gene within the cell sample; and (d) determining whether the cell sample exhibits an altered cell proliferative, whereby a response identifies a SynMuv gene.

In another aspect, the invention features a method of identifying a SynMuv gene in a cell, involving: (a) providing a preparation of cellular DNA (for example, from the human genome or a cDNA library (such as a cDNA library isolated from a cell type that is cancerous); (b) providing a detectably-labelled DNA sequence (for example, prepared by the methods of the invention) having homology to a conserved region of a SynMuv gene; (c) contacting the preparation of cellular DNA with the detectably-labelled DNA sequence under hybridization conditions providing detection of genes having 50% nucleotide or greater sequence identity; and (d) identifying a SynMuv gene by its association with the detectable label.

In another aspect, the invention features a method of isolating a SynMuv gene from a recombinant library, involving: (a) providing a recombinant library; (b) contacting the library with a detectably-labelled gene fragment produced according to the PCR method of the invention under hybridization conditions providing detection of genes having 50% or greater nucleotide sequence identity; and (c) isolating a SynMuv gene by its association with the detectable label.

In another aspect, the invention features a method of identifying a SynMuv gene involving: (a) providing a cell tissue sample; (b) introducing by transformation into the cell sample a candidate SynMuv gene; (c) expressing the candidate SynMuv gene within the cell sample; and (d) determining whether the cell sample exhibits alteration in cell proliferation, whereby a change in (i.e. modulation of) cell proliferation identifies a SynMuv gene.

Preferably, the cell sample is a cell type which may be assayed for proliferation or a SynMuv phenotype; the candidate SynMuv gene is obtained from a cDNA expression library; and the phenotype involves cell proliferation.

In another aspect, the invention features a method of modulating cell proliferation in an animal wherein the method includes: (a) providing DNA encoding at least one SynMuv polypeptide to a cell; wherein the DNA is integrated into the genome of the cell and is positioned for expression in the cell; and the SynMuv gene is under the control of regulatory sequences suitable for controlled expression of the gene(s); wherein the SynMuv transgene is expressed at a level sufficient to affect cell proliferation relative to a cell lacking the SynMuv transgene. It will be appreciated that SynMuv polypeptides also may be administered directly to modulating cell proliferation.

In a related aspect, the invention features a method of modulating cell proliferation wherein the method involves: (a) producing a cell having integrated in the genome a transgene containing the SynMuv gene under the control of a promoter providing constitutive expression of the SynMuv gene.

In yet another related aspect, the invention features a method of modulating cell death wherein the method involves: (a) producing a cell having integrated in the genome a transgene containing the SynMuv gene under the control of a promoter providing controllable expression of the SynMuv gene; and (b) regulating the environment of the cell so that the SynMuv transgene is controllably expressed in the cell. In preferred embodiments, the SynMuv gene is expressed using a tissue-specific or cell type-specific promoter, or by a promoter that is activated by the introduction of an external signal or agent, such as a chemical signal or agent.

In a related aspect, the invention provides a method of modulating cell proliferation in an animal by providing an cell proliferation modulation amount of SynMuv polypeptide.

In another aspect, the invention features a purified antibody which binds specifically to a SynMuv family protein. Such an antibody may be used in any standard immunodetection method for the identification of a SynMuv polypeptide. Preferably, the antibody binds specifically to lin-37, lin35, lin-53, lin-55, lin-52, lin-54, or C.elegans E2F-1. In various embodiments the antibody may react with other SynMuv polypeptides or may be specific for one or a few SynMuv polypeptides. The antibody may be a monoclonal polyclonal antibody.

In another aspect, the invention features a method of identifying a compound which modulates cell proliferation. The method includes (a) providing a cell expressing a polypeptide; and (b) contracting the cell with a candidate compound, and monitoring the expression of a SynMuv gene. An alteration in the level of expression of the SynMuv gene indicates the presence of a compound which modulates cell proliferation. The compound may be an inhibitor or an enhancer of cell proliferation.

By "SynMuv gene" is meant a gene encoding a polypeptide which modulates cell death (inhibiting or enhancing) in a cell or tissue when provided by other intracellular or extracellular delivery methods. In preferred embodiments the SynMuv gene is a gene having about 50% or greater nucleotide sequence identity to at least one of the SynMuv amino acid encoding sequences of FIG. 2, 4, 6, 8, 9, 11, or 13 or encoded by the sequence of FIG. 26 or FIG. 27, or portions thereof.

By an "SynMuv gene" is also meant any member of the family of genes characterized by their ability to modulate cell proliferation and having at least 110%, preferably 30%, and most preferably 50% amino acid sequence identity to at least one of the SynMuv protein described herein below. Representative members of the SynMuv gene family include, the lin-37, lin-35, lin-53, lin-55, lin-52, lin-54, and E2F-1 gene of C.elegans, and the lin-54 genes of the mouse and human.

lin-54 genes of the invention, in particular, may alternatively be identified as encoding a protein having at least 40% identity to the boxed region in FIG. 13 and encoding at least one of the cystein motifs shown in Section VIII, below.

Specifically excluded from the SynMuv genes of the invention are known retinoblastoma tumor suppressor pathway genes, including the Rb gene, in all species; p107, in human and mouse; and p130 in humans. Also excluded are known E2F genes, including human, murine, and drosphila human E2F genes (e.g., E2F-1, E2F-2, E2F-3, E2F-4, E2F-5, E2F-6).

By "SynMuv protein" is meant a polypeptide encoded by a SynMuv gene.

By "modulating cell proliferation" or "altering cell proliferation" is meant increasing or decreasing the number of cells which undergo cell division in a given cell population or altering the fate of a given cell. It will be appreciated that the degree of modulation provided by a SynMuv or modulating compound in a given assay will vary, but that one skilled in the art can determine the statistically significant change in the level of cell proliferation which identifies a SynMuv or a compound which modulates a SynMuv.

By "inhibiting cell proliferation" is meant any decrease in the number of cells which undergo division relative to an untreated control. Preferably, the decrease is at least 25%, more preferably the decrease is 50%, and most preferably the decrease is at least one-fold.

By "polypeptide" is meant any chain of amino acids, regardless of length or post-translational modification (e.g., glycosylation or phosphorylation).

By "substantially identical" is meant a polypeptide or nucleic acid exhibiting at least 50%, preferably 85%, more preferably 90%, and most preferably 95% homology to a reference amino acid or nucleic acid sequence. For polypeptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 50 nucleotides, preferably at least 60 nucleotides, more preferably at least 75 nucleotides, and most preferably 110 nucleotides.

Sequence identity may be measured using sequence analysis software on the default setting (i.e., Sequence Analysis Software Package of the Genetics Computer Group, University of Wisconsin Biotechnology Center, 1710 University Avenue, Madison, Wis. 53705). Such software may match similar sequences by assigning degrees of homology to various substitutions, deletions, and other modifications. Conservative substitutions typically include substitutions within the following groups: glycine, alanine, valine, isoleucine, leucine; aspartic acid, glutamic acid, asparagine, glutamine; serine, threonine; lysine, arginine; and phenylalanine, tyrosine.

By a "substantially pure polypeptide" is meant a SynMuv polypeptide which has been separated from components which naturally accompany it. Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, SynMuv polypeptide. A substantially pure SynMuv polypeptide may be obtained, for example, by extraction from a natural source (e.g., a fibroblast, neuronal cell, or lymphocyte cell); by expression of a recombinant nucleic acid encoding a SynMuv polypeptide; or by chemically synthesizing the protein. Purity can be measured by any appropriate method, e.g., those described in column chromatography, polyacrylamide gel electrophoresis, or by HPLC analysis.

A protein is substantially free of naturally associated components when it is separated from those contaminants which accompany it in its natural state. Thus, a protein which is chemically synthesized or produced in a cellular system different from the cell from which it naturally originates will be substantially free from its naturally associated components. Accordingly, substantially pure polypeptides include those derived from eukaryotic organisms but synthesized in *E. coli* or other prokaryotes.

By "substantially pure DNA" is meant DNA that is free of the genes which, in the naturally-occurring genome of the organism from which the DNA of the invention is derived, flank the gene. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence.

By "transformed cell" is meant a cell into which (or into an ancestor of which) has been introduced, by means of recombinant DNA techniques, a DNA molecule encoding (as used herein) a SynMuv polypeptide.

By "transgene" is meant any piece of DNA which is inserted by artifice into a cell, and becomes part of the genome of the organism which develops from that cell. Such a transgene may include a gene which is partly or entirely heterologous (i.e., foreign) to the transgenic organism, or may represent a gene homologous to an endogenous gene of the organism. Self replicating units, such as artificial chromosomes, are included.

By "transgenic" is meant any cell which includes a DNA sequence which is inserted by artifice into a cell and becomes part of the genome of the organism which develops from that cell. As used herein, the transgenic organisms are generally transgenic nematodes or mammals (e.g., C.elegans rodents such as rats or mice) and the DNA (transgene) is inserted by artifice into the nuclear genome.

By "transformation" is meant any method for introducing foreign molecules into a cell. Microinjection, lipofection, calcium phosphate precipitation, retroviral deliver, electroporation and biolistic transformation are just a few of the teachings which may be used. For example, Biolistic transformation is a method for introducing foreign molecules into a cell using velocity driven microprojectiles such as tungsten or gold particles. Such velocity-driven methods originate from pressure bursts which include, but are not limited to, helium-driven, air-driven, and gunpowder-driven techniques. Biolistic transformation may be applied to the transformation or transfection of a wide variety of cell types and intact tissues including, without limitation, intracellular organelles (e.g., and mitochondria and chloroplasts), bacteria, yeast, fungi, algae, animal tissue, and cultured cells.

By "positioned for expression" is meant that the DNA molecule is positioned adjacent to a DNA sequence which directs transcription and translation of the sequence (i.e., facilitates the production of, e.g., a SynMuv polypeptide, a recombinant protein or a RNA molecule).

By "reporter gene" is meant a gene whose expression may be assayed; such genes include, without limitation, β-glucuronidase (GUS), luciferase, chloramphenicol transacetylase (CAT), and β-galactosidase.

By "promoter" is meant minimal sequence sufficient to direct transcription. Also included in the invention are those promoter elements which are sufficient to render promoter-dependent gene expression controllable for cell-type specific, tissue-specific or inducible by external signals or agents; such elements may be located in the 5' or 3' regions of the native gene.

By "operably linked" is meant that a gene and a regulatory sequence(s) are connected in such a way as to permit gene expression when the appropriate molecules (e.g., transcriptional activator proteins) are bound to the regulatory sequence(s).

By "conserved region" is meant any stretch of six or more contiguous amino acids exhibiting at least 30%, preferably 50%, and most preferably 70% amino acid sequence identity between two or more homologs of a SynMuv family member, (e.g., human LIN-54, and nematode LIN-54).

By "detectably-labelled" is meant any means for marking and identifying the presence of a molecule, e.g., an oligonucleotide probe or primer, a gene or fragment thereof, or a cDNA molecule. Methods for detectably-labelling a molecule are well known in the art and include, without limitation, radioactive labelling (e.g., with an isotope such as $^{32}P$ or $^{35}S$) and nonradioactive labelling (e.g., chemiluminescent labelling, e.g., fluorescein labelling).

By "purified antibody" is meant antibody which is at least 60%, by weight, free from proteins and naturally-occurring organic molecules with which it is naturally associated. Preferably, the preparation is at least 75%, more preferably 90%, and most preferably at least 99%, by weight, antibody, e.g., a SynMuv specific antibody. A purified antibody may be obtained, for example, by affinity chromatography using recombinantly-produced protein or conserved motif peptides and standard techniques.

By "specifically binds" is meant an antibody which recognizes and binds a protein but which does not substantially recognize and bind other molecules in a sample, e.g., a biological sample, which naturally includes protein.

Other features and advantages of the invention will be apparent from the following description of the preferred embodiments thereof, and from the claims.

BRIEF DESCRIPTION OF THE DRAWINGS

FIG. 2 shows the LIN-37 protein sequence (SEQ ID NO: 1).

FIG. 3 shows the lin-37 cDNA sequence (SEQ ID NO:2).

FIG. 4 shows the LIN-35 protein sequence (SEQ ID NO:3).

FIG. 5 shows the lin-35 cDNA sequence (SEQ ID NO:4).

FIG. 6 shows the LIN-53 protein sequence (SEQ ID NO:5).

FIG. 7 shows the lin-53 cDNA sequence (SEQ ID NO:6).

FIG. 8 shows the partial LIN-55 protein sequence (SEQ ID NO:7) and the lin-55 cDNA sequence (SEQ ID NO:8).

FIG. 9 shows the C. elegans E2F-1 protein sequence (SEQ ID NO:9).

FIG. 10 shows the C. elegans E2F-1 cDNA sequence (SEQ ID NO: 10).

FIG. 11 shows the LIN-52 protein sequence (SED ID No: 11).

FIG. 12 shows the lin-52 cDNA sequence (SEQ ID No:12).

FIG. 13 shows the LIN-54 protein sequence (SEQ ID NO: 13).

FIG. 14 shows the lin-54 cDNA sequence (SEQ ID NO: 14).

FIG. 25 shows a diagram of the strategy for detection of additional SynMuv alleles.

FIG. 26 shows the sequence of the M. musculus cDNA homolog of lin-54 (SEQ ID NO: 15).

FIG. 27 shows the sequence of the H. sapiens cDNA homolog of lin-54 (SEQ ID NO: 16).

DETAILED DESCRIPTION OF THE INVENTION

I. Introduction

Figure 1:
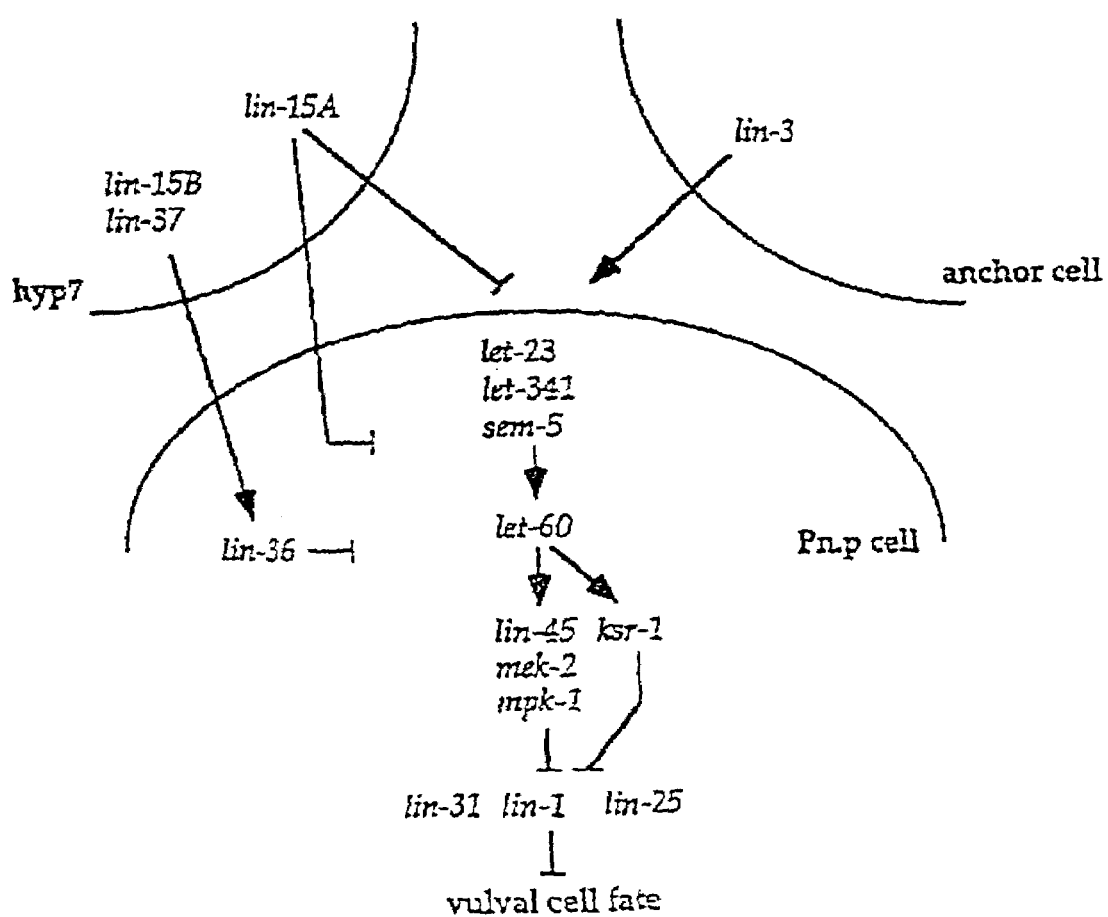
FIG. 1 shows a schematic of a model for synthetic multivulva gene action.
Figure 15:
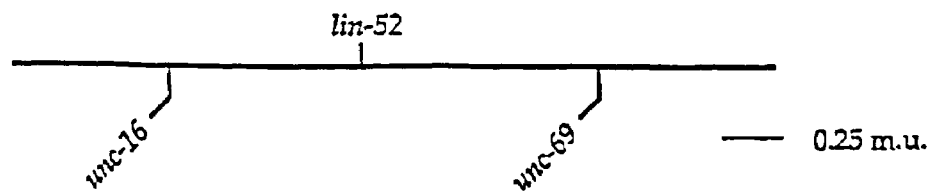
FIG. 15 shows a map of the position of lin-52 on LGIII.

We have now cloned lin-37, lin-35, and lin-53 and lin-55. Data obtained from cloning indicates that the class B genes constitute a tumor suppressor pathway. Accordingly, the synMuv pathway genes, the encoded proteins, and the worms described herein may be used to identify new tumor suppressors in other species, such as mammals, and may be used to identify therapeutic compounds. FIG. 1 illustrates the placement of our novel genes within the synMuv pathway.

lin-37 encodes a novel protein and as with the other synMuv genes cloned and described herein the invention provides the gene, the protein, and mutants derived therefrom (FIG. 2, SEQ ID NO 1 and FIG. 3, SEQ ID NO 2, respectively.)

lin-35 has also been cloned. FIG. 4 provides the LIN-34 protein sequence (SEQ 3) and FIG. 5 provides the lin-34 sequence (SEQ 4). The cloning of lin-35 has shed light on how the class B synMuv genes act to negatively regulate vulval induction. lin-35 encodes a homolog of the mammalian pocket protein family, which includes retinoblastoma protein (Rb), p107, and p130. This family of proteins has been the subject of intense study since the cloning of Rb in 1986. Rb is a tumor suppressor gene, that is, mutations that inactivate Rb predispose individuals to tumor formation. Most commonly, inactivation of Rb results in a rare eye cancer, retinoblastoma, although inactivating mutations in Rb have been found in other types of tumors. The RB protein is thought to function as a negative regulator of cell cycle progression. A number of molecules which interact, both directly and indirectly, with Rb and the other pocket proteins have been characterized in mammalian cells.

Our cloning of lin-53 (FIGS. 5 and 7) indicates that lin-53 encodes a homolog of p48, a protein which has been shown to bind Rb. Although the functional significance of the interaction between p48 and Rb is not fully understood, recent studies suggest p48 may play a role in remodeling chromatin structure.

We have also cloned lin-55 (FIG. 8) and found that it encodes a homolog of the DP family of proteins. DP family members, together with E2F proteins, bind DNA at specific sites, thereby regulating the transcription of genes that are essential for cell cycle progression. Pocket proteins such as Rb bind to the DP-E 2F complex to repress transcription.

We have also cloned lin-52 (FIGS. 11 and 12) and lin-54 (FIGS. 13 and 14). Like lin-37, these genes do not have homology to known tumor suppressor genes. We searched public sequence databases and found human and mouse cDNA clones that are similar to lin-54. We have isolated more cDNA clones of the human gene and found that its region of similarity extends beyond the sequence found in public databases. Due to the sequence similarity, we speculate that lin-54 shares some common function with the human and mouse genes.

We have also found an E2F-like gene in worms (FIGS. 9 and 10). This gene, which we are referring to as C. elegans E2F-1, was identified because of its similarity to mammalian E2F genes. We have conducted experiments, which are described below, that suggest that C. elegans E2F-1 is a member of the worm synMuv genetic pathway. To summarize, the synMuvs act to negatively regulate vulval induction. At a molecular level, vulval induction is controlled by a Ras pathway. Ras pathway members have been shown to mutate in a variety of human cancers to give an increased level of pathway signalling. We have now shown that a pathway related to the tumor suppressor Rb negatively regulates Ras pathway signalling. We have also identified a number of molecules which act as part of this Rb-related pathway. The striking parallel between the Rb pathway in mammals and the Rb-related pathway we have discovered in worms indicates that further characterization of the synthetic multivulva genes and their mammalian homologs, where appropriate, will provide insight into how cell proliferation is regulated in mammals, particularly humans.

Experiments which stem directly from this research include searches for mammalian homologs of the novel synMuv genes. Such homologs may function in activating, enhancing, or otherwise intensifying the effects of tumor suppressors or oncogenes in mammals.

Genetic enhancer or suppressor screens may be performed to identify new genes which may function in/or initiating, enhancing, otherwise interfacing with this Rb-related pathway. In addition, knowing the association provided herein between the synMuv genes and proliferative disease pathways in mammals, one skilled in the art can readily devise drug screens to search for compounds that affect cell proliferation. Specifically, compounds which block the Muv phenotype of synMuv mutant animals are potential antitumor agents. Compounds which stimulate cell division in animals with a single, silent synMuv mutation are likely to be agonists of cell proliferation and may act in a manner analogous to growth factors.

By providing insight regarding the function of the SynMuv genes in tumor suppression, Applicants have provided, in concert with generally known molecular biology and nematodes genetic methods, the necessary elements of such methods and the compounds required for the practice of such methods.

II. Model for synMuv Action

FIG. 1 shows the sites of action of the synMuv genes and the lines indicate sites of negative regulation of the Ras pathway that mediates vulval induction.

III. Cloning of Lin-52.

lin-52 has been cloned and it encodes a novel predicted protein of amino acids (FIGS. 11 and 12). The n771 allele contains a missense mutation in the gene. Reverse-transcriptase-polymerase chain reaction (RT-PCR) analysis of this gene reveals that its RNA is SL2 trans-spliced. SL2 trans-splicing is found most often in RNA from the downstream genes of C. elegans operons.

Figure 8:
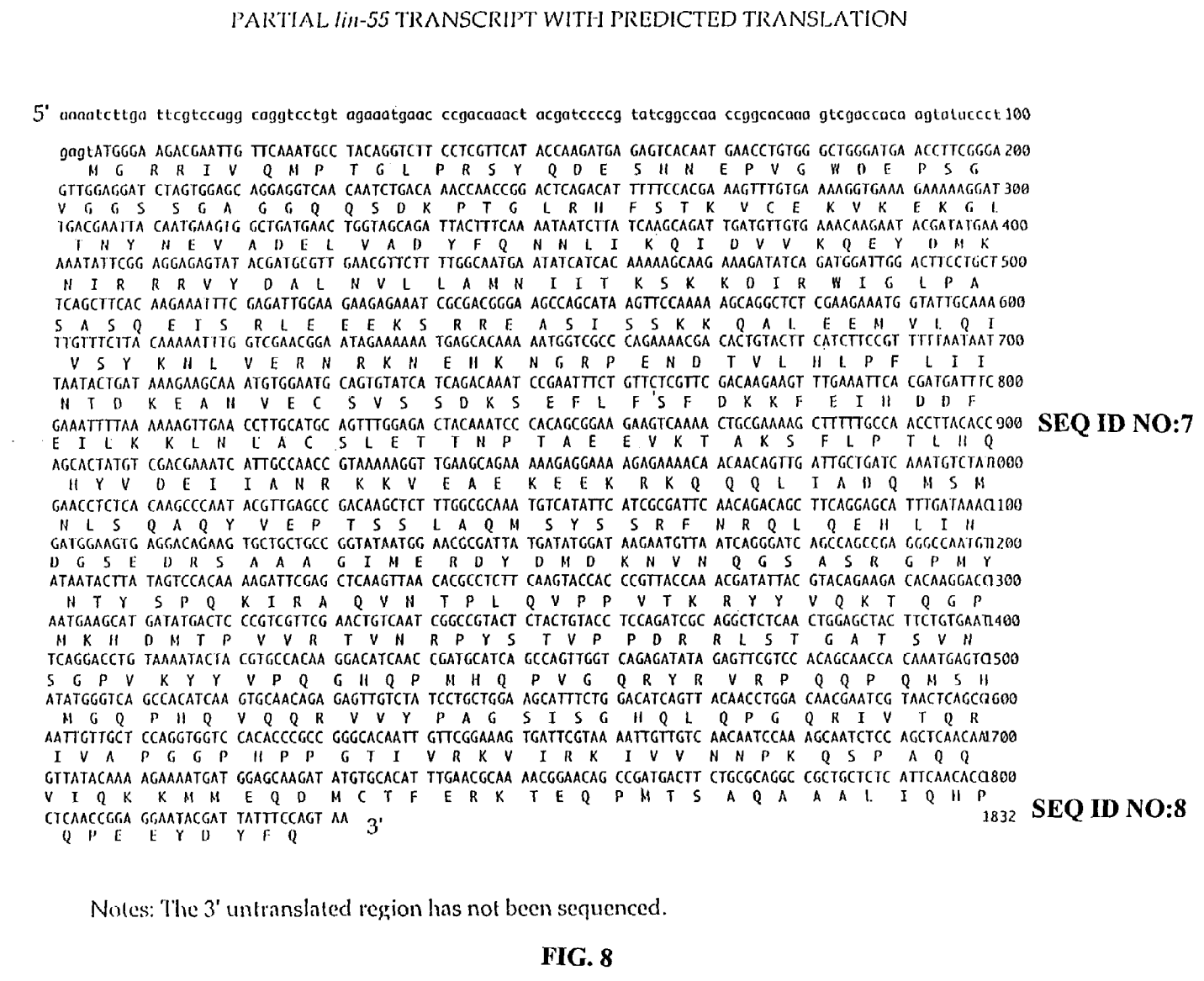
Figure 16:
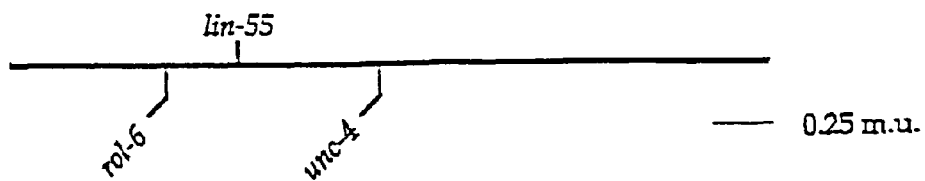
FIG. 16 shows a map of the position of lin-55 on LGII.

IV. Cloning of Lin-55 lin-55 maps on LGII between rol-6 and unc-4, we first obtained cosmid rescue and identified a candidate gene (FIG. 16). We then proceeded to clone the gene. lin-55 encodes a protein similar to DP protein family members (FIG. 8). A single mutant allele of lin-55, n2994, has been identified. Deficiency studies indicate that the allele results in a partial reduction of LIN-55 function.

V. Cloning of Lin-37

Figure 17:
FIG. 17 shows a picture of an RNA blot demonstrating that lin-37 massage is present in both embryonic and mixed stage RNAs.

The lin-37 transcript is approximately 1 kb in size (FIG. 3) and is present both in embryonic and mixed-staged RNAs as revealed by Northern analysis (FIG. 17). A cDNA isolated from the Okkema embryonic cDNA library is about 950 bp in size and can rescue the lin-37 Muv phenotype when expressed under the control of the col-10 promoter. (col-10 encodes a cuticle collagen and is highly expressed in the hypodermis and its precursor cells.) The predicted polypeptide product of 31.5 kD is novel. We have now determined the sequence of the coding region of the two existing lin-37 alleles (FIG. 18). n758 contains a splice donor mutation in the first intron and is likely to be a null allele. n2234 contains a nonsense mutation in the middle of the coding sequence. A lin-37::GFP transgene is expressed broadly in embryos and in hypodermal cells and vulval cells throughout larval development, consistent with its cell-nonautonomous site of action (FIG. 19; Hedgecock and Herman, Genetics 141: 989–1006, 1995).

Figure 18:
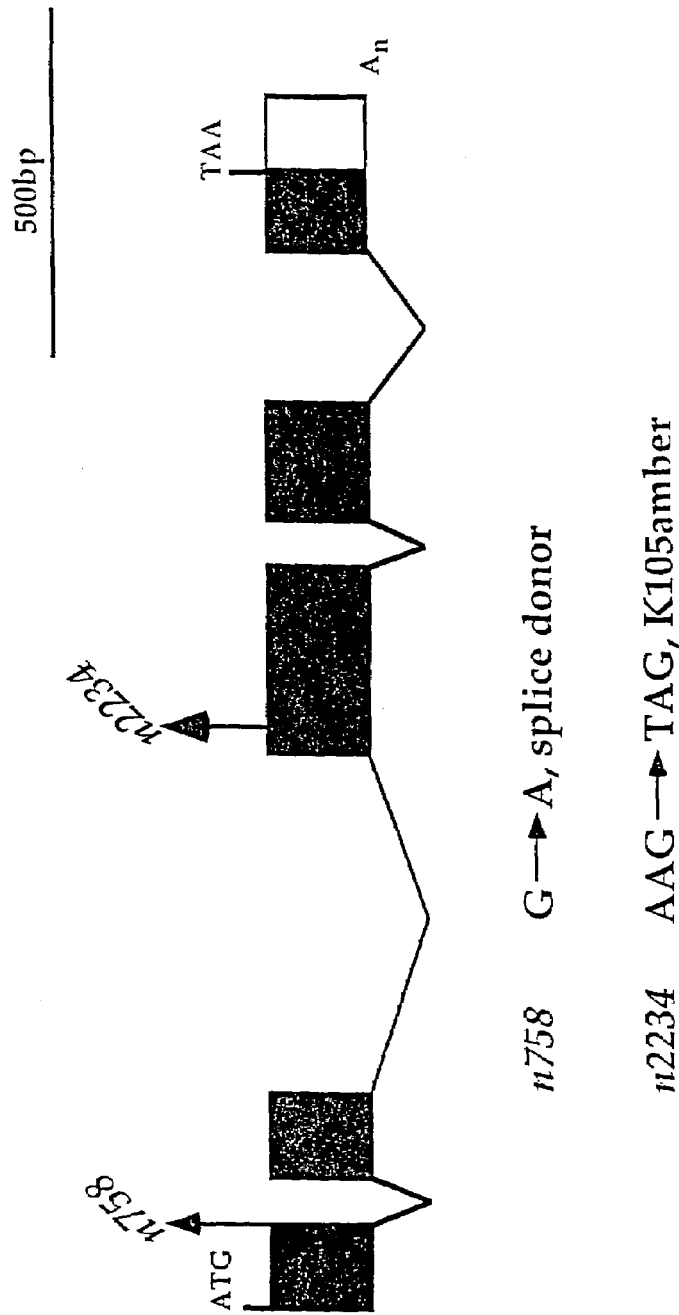
FIG. 18 shows a diagram of the lin-37 gene structure and the positions of n758 and n2234.
Figure 19:
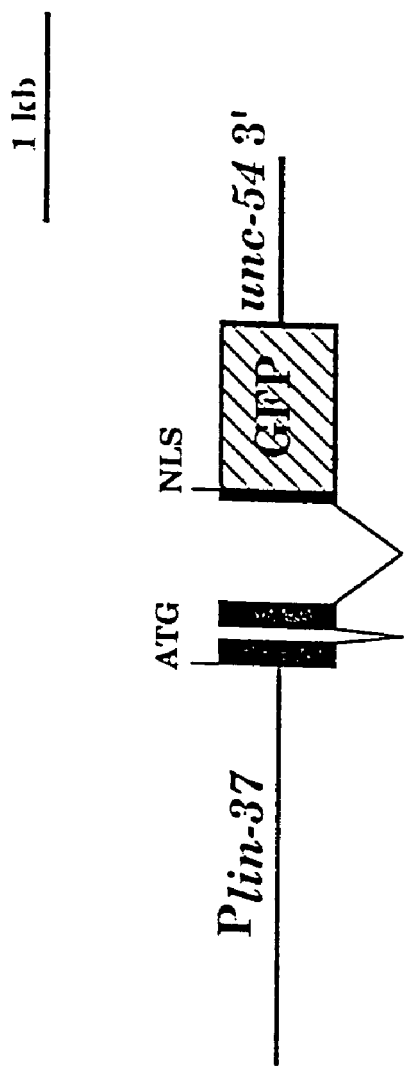
FIG. 19 shows a diagram of lin-37:: GFP fusion.
Figure 20:
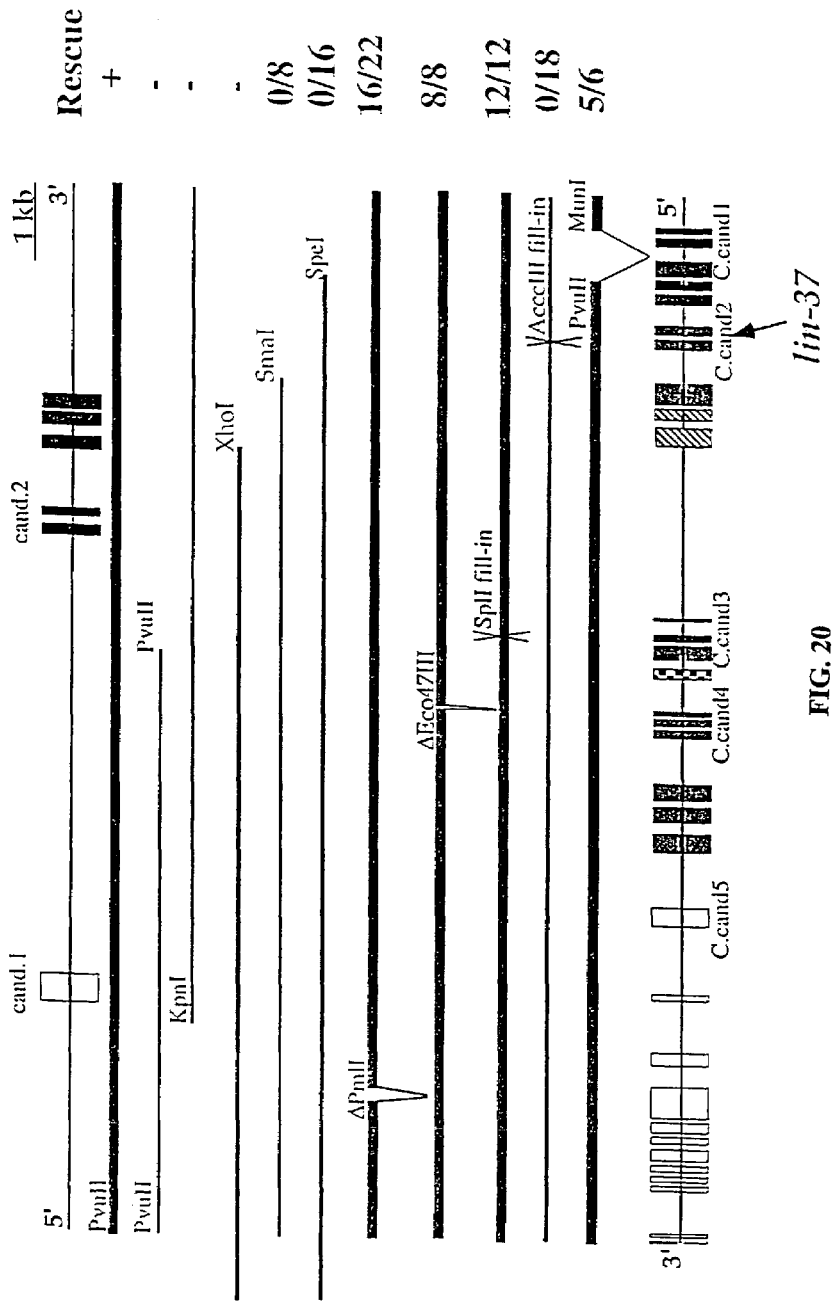
FIG. 20 shows a diagram of constructs used for lin-37 rescues.
Figure 21:
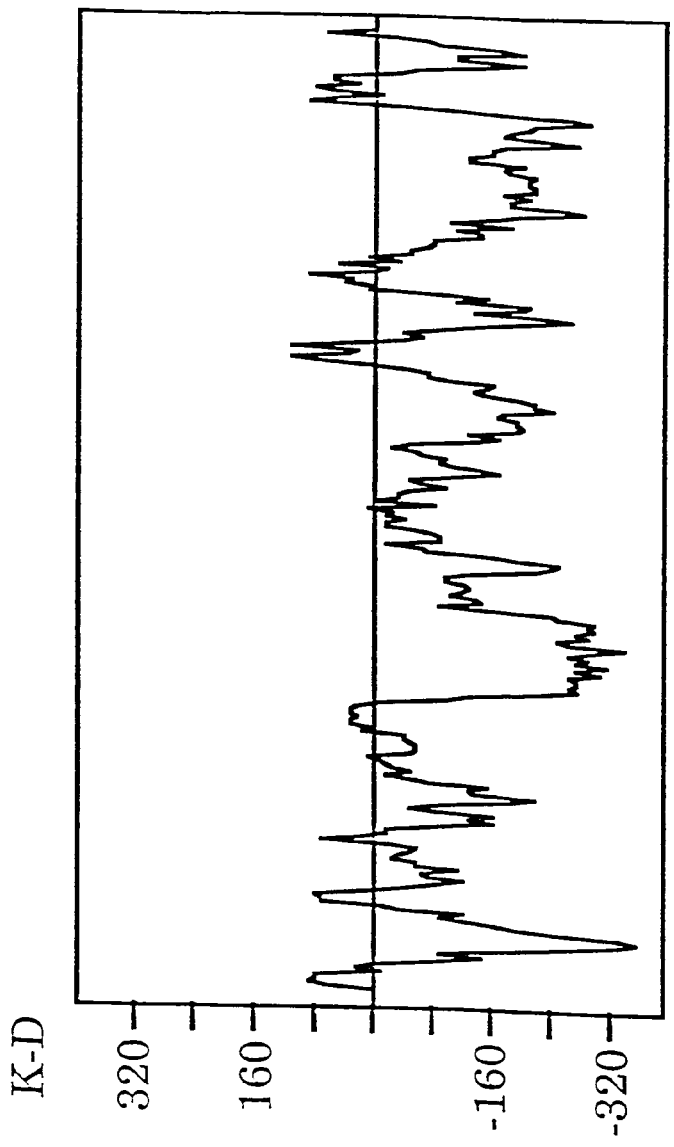
FIG. 21 shows a chart of LIN-37 hydrophobicity.
Figure 22:
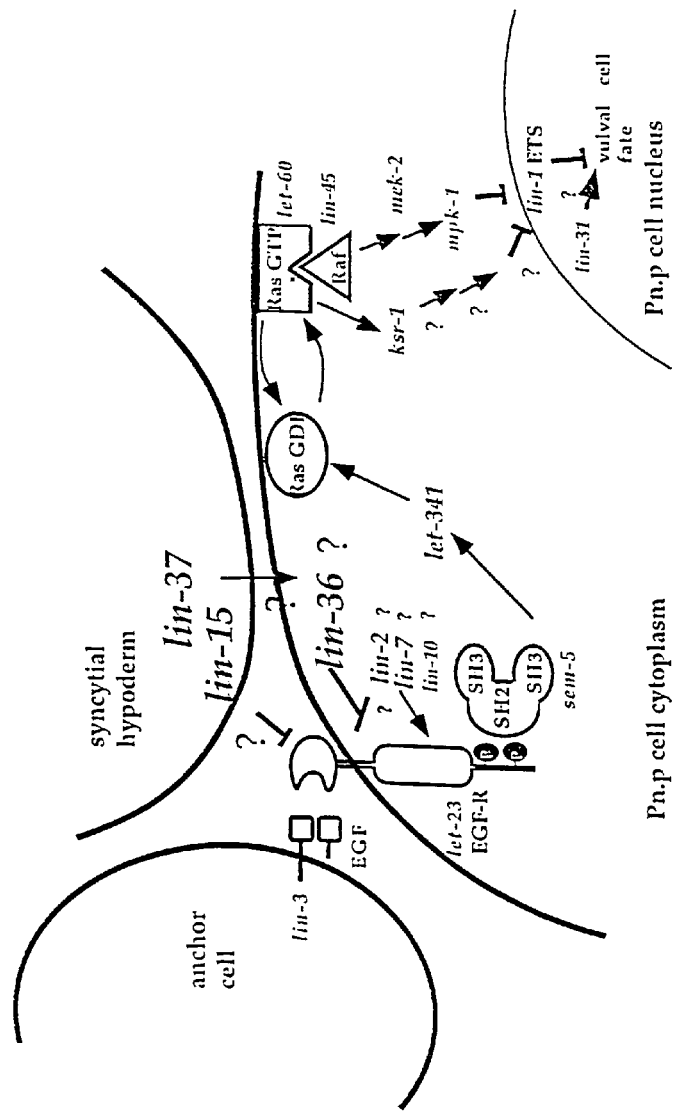
FIG. 22 shows a diagram of a model for lin-37 function.

FIG. 20 shows the rescue of lin-37; FIG. 18 shows the lin-37 structure; FIG. 21 shows that lin-37 encodes a novel 32 kD hydrophilic protein; and FIG. 22 shows a model for lin-37 function.

VI. Cloning of Lin-35 and Lin-53

We have also rescued lin-35 and lin-53 and protein sequences for lin-35, lin-37 and lin-53.

lin-53 is a complex locus containing two transcription units under the control of the same promoter. The 5' transcript is referred to as lin-53 because it is mutated in lin-53 mutants, the 3' transcript is about 200 bp apart and encodes a protein 70% identical to the lin-53 transcription unit and could be functionally related.

The genomic sequence provided does not contain the promoter region or the first exon of lin-53 cDNA. These sequences may, however, be readily obtained using standard cloning techniques.

VII. Identification and Functional Characterization of C.elegans E2F-1

We have identified a partial C. elegans cDNA clone that shares similarity with E2F family members. We used this clone to obtain full-length cDNA clones of this gene, which we are calling C.elegans E2F-1 (FIG. 10). We have not identified any mutations in C.elegans E2F-1 but we have conducted experiments that suggest it may function in the worm synMuv pathway. Specifically, we have used a technique referred to as "RNA inhibition" to assess the loss-of-function phenotype of C.elegans E2F-1. When injected into adult worms, RNA derived from specific gene can inactivate, by an unknown mechanism, the same gene in the progeny of the injected worm. We injected C.elegans E2F-1 RNA into adult worms and found it causes a synthetic Muv phenotype in the progeny of injected worms. One may now screen for a deletion mutation in the C.elegans E2F-1 gene using this phenotype to determine if it also causes a synthetic Muv phenotype.

VIII. Cloning of Lin-54 and Identification of Human and Mouse Lin-54-Like Genes lin-54 was cloned by standard transformation rescue. It encodes a predicted protein of 438 amino acids (FIGS. 13 and 14). The two alleles of this gene, n2231 and n2990, are both missense mutations.

In search of public sequence databases, we found human and mouse cDNA clones that are derived from genes similar to lin-54 (FIGS. 26 and 27). We have subsequently isolated more cDNA clones of the human gene in order to build a complete open reading frame for this gene. Thus far we have an open reading frame that is 3.5 kilobases in length. If translated, the human and mouse genes encode proteins that are similar to LIN-54 in a cysteine-rich domain. Within this domain there appear to be two cysteine repeats with the following signatures, where X denotes an amino acid other than cysteine:

C X C $X_4$ C$X_4$ C X C$X_6$ C $X_2$C X C$X_2$ C SEQ ID NO: 16 and

C X C $X_4$ C$X_4$C X C$X_6$ C$X_3$C X C $X_2$C SEQ ID NO: 17

Although the molecular functions of LIN-54 and these human and mouse proteins are unknown, we believe that the high degree of sequence identity in the cysteine-rich domain indicates that the proteins share a common molecular function.

IX. Characterization of Interactions Among the SynMuv Genes.

Standard yeast 2-hybrid techniques are used to characterize the physical interactions between the synMuv gene products. These 2 hybrid systems can also be used to detect therapeutic compounds which disrupt the synMuv protein—protein interactions. We have performed two-hybrid analyses with lin-9, lin-15A, lin-15B and lin-36 and found that the LIN-36 protein may self-associate but that none of the other proteins appear to interact with each other. The array in FIG. 23 to shows these results.

Figures 23, 24:
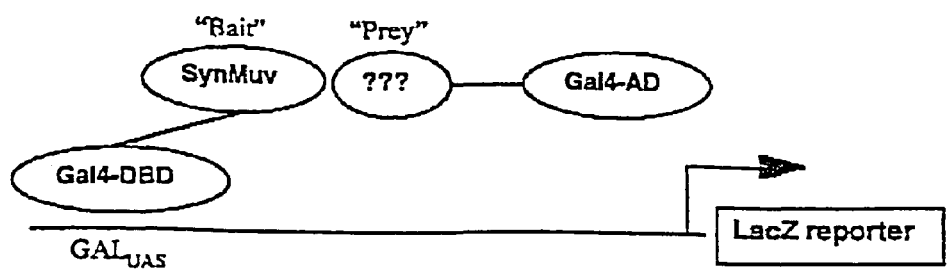
FIG. 23 shows a diagram of data obtained using LIN-36, LIN-9, LIN-15A, LIN-15B and SNP1 (as a control) in a protein—protein binding assay.
FIG. 24 shows a picture of the strategy for characterization of molecular interaction of the SynMuv gene products.

To further study the protein—protein interactions we have constructed the genetic screen shown in FIG. 24.

This screen should detect synMuv B class mutations which, in combination with a A class mutation, may be lethal to the animal or may cause the animal to be sterile. Some synMuv B alleles are sterile without a class A mutation in the background. A screen using these mutations would give rise to $A^-$; $B^-$, Muv animals where the $B^-$ mutation confers sterility.

Using this observation we have also constructed a genetic screen based upon the sterility phenotypes to identify more synMuv genes. This strategy is shown in FIG. 25.

X. SynMuv Protein Expression

SynMuv genes may be expressed in both prokaryotic and eukaryotic cell types. For those SynMuv's which modulate cell proliferation it may be desirable to express the protein under control of an inducible promotor for the purposes of protein production.

In general, SynMuv proteins according to the invention may be produced by transformation of a suitable host cell with all or part of a SynMuv-encoding cDNA fragment (e.g., the cDNA described above) in a suitable expression vehicle.

Those skilled in the field of molecular biology will understand that any of a wide variety of expression systems may be used to provide the recombinant protein. The precise host cell used is not critical to the invention. The SynMuv protein may be produced in a prokaryotic host (e.g., *E. coli*) or in a eukaryotic host (e.g., nematodes, Saccharamyces cerevisiae, insect cells, e.g., Sf21 cells, or mammalian cells, e.g., COS 1, NIH 3T3, or HeLa cells). Such cells are available from a wide range of sources (e.g., the American Type Culture Collection, Rockland, Md.; also, see, e.g., Ausubel et al., *Current Protocols in Molecular Biology*, John Wiley & Sons, New York, 1994). The method of transformation or transfection and the choice of expression vehicle will depend on the host system selected. Transformation and transfection methods are described, e.g., in Ausubel et al., (supra); expression vehicles may be chosen from those provided, e.g., in *Cloning Vectors: A Laboratory Manual* (P. H. Pouwels et al., 1985, Supp. 1987).

One preferred expression system is the baculovirus system (using, for example, the vector pBacPAK9) available from Clontech (Palo Alto, Calif.). If desired, this system may be used in conjunction with other protein expression techniques, for example, the myc tag approach described by Evan et al. (Mol. Cell Biol. 5:3610–3616, 1985).

Alternatively, a SynMuv protein is produced by a stable-transfected mammalian cell line. A number of vectors suitable for stable transfection of mammalian cells are available to the public, e.g., see Pouwels et al. (supra); methods for constructing such cell lines are also publicly available, e.g., in Ausubel et al. (supra). In one example, cDNA encoding the SynMuv protein is cloned into an expression vector which includes the dihydrofolate reductase (DHFR) gene. Integration of the plasmid and, therefore, the SynMuv protein-encoding gene into the host cell chromosome is selected for by inclusion of 0.01–300 μM methotrexate in the cell culture medium (as described in Ausubel et al., supra). This dominant selection can be accomplished in most cell types. Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHFR and pAdD26SV(A) (described in Ausubel et al., supra). Any of the host cells described above or, preferably, a DHFR-deficient CHO cell line (e.g., CHO DHFR⁻ cells, ATCC Accession No. CRL 9096) are among the host cells preferred for DHFR selection of a stable-transfected cell line or DHFR-mediated gene amplification.

Once the recombinant SynMuv protein is expressed, it is isolated, e.g., using affinity chromatography. In one example, an anti-SynMuv protein antibody (e.g., produced as described herein) may be attached to a column and used to isolate the SynMuv protein. Lysis and fractionation of SynMuv protein-harboring cells prior to affinity chromatography may be performed by standard methods (see, e.g., Ausubel et al., supra).

Once isolated, the recombinant protein can, if desired, be further purified, e.g., by high performance liquid chromatography (see, e.g., Fisher, *Laboratory Techniques In Biochemistry And Molecular Biology*, eds., Work and Burdon, Elsevier, 1980).

Polypeptides of the invention, particularly short SynMuv protein fragments, can also be produced by chemical synthesis (e.g., by the methods described in *Solid Phase Peptide Synthesis,* 2nd ed., 1984 The Pierce Chemical Co., Rockford, Ill.).

These general techniques of polypeptide expression and purification can also be used to produce and isolate useful SynMuv fragments or analogs (described herein).

XI. Anti-SynMuv Antibodies

To generate SynMuv-specific antibodies, a SynMuv coding sequence can be expressed as a C-terminal fusion with glutathione S-transferase (GST) (Smith et al., Gene 67:31–40, 1988). The fusion protein can be purified on glutathione-Sepharose beads, eluted with glutathione cleaved with thrombin (at the engineered cleavage site), and purified to the degree necessary for immunization of rabbits. Primary immunizations can be carried out with Freund's complete adjuvant and subsequent immunizations with Freund's incomplete adjuvant. Antibody titres are monitored by Western blot and immunoprecipitation analyses using the thrombin-cleaved SynMuv protein fragment of the GST-SynMuv fusion protein. Immune sera are affinity purified using CNBr-Sepharose-coupled SynMuv protein. Antiserum specificity is determined using a panel of unrelated GST proteins (including GSTp53, Rb, HPV-16 E6, and E6-AP) and GST-trypsin (which was generated by PCR using known sequences).

As an alternate or adjunct immunogen to GST fusion proteins, peptides corresponding to relatively unique regions of SynMuv may be generated and coupled to keyhole limpet hemocyanin (KLH) through an introduced C-terminal lysine. Antiserum to each of these peptides is similarly affinity purified on peptides conjugated to BSA, and specificity tested in ELISA and Western blots using peptide conjugates, and by Western blot and immunoprecipitation using SynMuv expressed as a GST fusion protein.

Alternatively, monoclonal antibodies may be prepared using the SynMuv proteins described above and standard hybridoma technology (see, e.g., Kohler et al., Nature 256: 495, 1975; Kohler et al., Eur. J. Immunol. 6:511, 1976; Kohler et al., Eur. J. Immunol. 6:292, 1976; Hammerling et al., In Monoclonal Antibodies and T Cell Hybridomas, Elsevier, N.Y., 1981; Ausubel et al., supra). Once produced, monoclonal antibodies are also tested for specific SynMuv recognition by Western blot or immunoprecipitation analysis (by the methods described in Ausubel et al., supra). Antibodies which specifically recognize SynMuv are considered to be useful in the invention; such antibodies may be used, e.g., in an immunoassay to monitor the level of SynMuv produced by a animal (for example, to determine the amount or subcellular location of SynMuv).

Preferably, antibodies of the invention are produced using fragments of the SynMuv protein which lie outside highly conserved regions and appear likely to be antigenic, by criteria such as those provided by the Peptidestructure program of the Genetics Computer Group Sequence Analysis Package (Program Manual for the GCG Package, Version 7, 1991) using the algorithm of Jameson and Wolf (CABIOS 4:181 1988)). In one specific example, such fragments are generated by standard techniques of PCR and cloned into the pGEX expression vector (Ausubel et al., supra). Fusion proteins are expressed in *E. coli* and purified using a glutathione agarose affinity matrix as described in Ausubel et al. (supra). To attempt to minimize the potential problems of low affinity or specificity of antisera, two or three such fusions are generated for each protein, and each fusion is injected into at least two rabbits. Antisera are raised by injections in a series, preferably including at least three booster injections.

XII. Identification of Molecules that Modulate SynMuv Protein Expression

Isolation of the SynMuv cDNAs also facilitates the identification of molecules which increase or decrease SynMuv expression. According to one approach, candidate molecules are added at varying concentrations to the culture medium of cells or nematodes expressing SynMuv mRNA. SynMuv expression is then measured, for example, by standard Northern blot analysis (Ausubel et al., supra) using a SynMuv cDNA (or cDNA fragment) as a hybridization probe (see also Table III). The level of SynMuv expression in the presence of the candidate molecule is compared to the level measured for the same cells in the same culture medium but in the absence of the candidate molecule. When nematodes are being used, use of the phenotypes associated with the SynMuv pathway may be used as the primary screen for alteration in protein expression.

If desired, the effect of candidate modulators on expression may, in the alternative, be measured at the level of SynMuv protein production using the same general approach and standard immunological detection techniques, such as Western blotting or immunoprecipitation with a SynMuv-specific antibody (for example, the SynMuv antibody described herein).

Candidate modulators may be purified (or substantially purified) molecules or may be one component of a mixture of compounds (e.g., an extract or supernatant obtained from cells; Ausubel et al., supra). In a mixed compound assay, SynMuv expression is tested against progressively smaller subsets of the candidate compound pool (e.g., produced by standard purification techniques, e.g., HPLC or FPLC) until a single compound or minimal compound mixture is demonstrated to modulate SynMuv expression.

Alternatively, or in addition, candidate compounds may be screened for those which modulate SynMuv cell death activity. In this approach, the degree of cell proliferation or the SynMuv phenotype in the presence of a candidate compound is compared to the degree of cell death in its absence, under equivalent conditions. Again, such a screen may begin with a pool of candidate compounds, from which one or more useful modulator compounds are isolated in a step-wise fashion. Cell death activity may be measured by any standard assay.

Candidate SynMuv modulators include peptide as well as non-peptide molecules (e.g., peptide or non-peptide molecules found, e.g., in a cell extract, mammalian serum, or growth medium on which mammalian cells have been cultured).

Modulators found to be effective at the level of SynMuv expression or activity may be confirmed as useful in animal models and, if successful, may be used as anti-cancer therapeutics for either the inhibition of cell death.

XIII. SynMuv Therapy

Because expression levels of SynMuv genes correlates with the levels of cell death, the SynMuv gene also finds use in gene therapy to modulate cell proliferation.

Retroviral vectors, adenoviral vectors, adeno-associated viral vectors, or other viral vectors with the appropriate tropism for cells likely to be involved in the cell proliferation disease may be used as a gene transfer delivery system for a therapeutic SynMuv gene construct. Numerous vectors useful for this purpose are generally known (Miller, Human Gene Therapy 15–14, 1990; Friedman, Science 244:1275–1281, 1989; Eglitis and Anderson, BioTechniques 6:608–614, 1988; Tolstoshev and Anderson, Current Opinion in Biotechnology 1:55–61, 1990; Sharp, The Lancet 337:1277–1278, 1991; Cornetta et al., Nucleic Acid Research and Molecular Biology 36:311–322, 1987; Anderson, Science 226:401–409, 1984; Moen, Blood Cells 17:407–416, 1991; and Miller and Rosman, Biotechniques 7:980–990, 1989; Le Gal La Salle et al., Science 259: 988–990, 1993; and Johnson, Chest 107:77S–83S, 1995). Retroviral vectors are particularly well developed and have been used in clinical settings (Rosenberg et al., N. Engl. J. Med 323:370, 1990; Anderson et al., U.S. Pat. No. 5,399, 346).

Non-viral approaches may also be employed for the introduction of therapeutic DNA into cells otherwise predicted to undergo insufficient or excess cell proliferation. For example, SynMuv may be introduced into a cell by the techniques of lipofection (Felgner et al., Proc. Natl. Acad. Sci. USA 84:7413, 1987; Ono et al., Neuroscience Lett 117:259, 1990; Brigham et al., Am. J. Med. Sci. 298:278, 1989; Staubinger and Papahadjopoulos, Meth. Enz. 101: 512, 1983); asialorosonucoid-polylysine conjugation (Wu and Wu, J. Biol. Chem. 263:14621, 1988; Wu et al., J. Biol. Chem. 264:16985, 1989); or, less preferably, microinjection under surgical conditions (Wolff et al., Science 247:1465, 1990).

For any of the above approaches, the therapeutic SynMuv DNA construct is preferably applied to the site of the predicted cell proliferation event (for example, by injection), but may also be applied to tissue in the vicinity of the predicted event or even to a blood vessel supplying the cells predicted to undergo insufficient or excess cell proliferation.

In the gene therapy constructs, SynMuv cDNA expression is directed from any suitable promoter (e.g., the human cytomegalovirus, simian virus 40, or metallothionein promoters), and its production is regulated by any desired regulatory element. For example, if desired, enhancers known to direct preferential gene expression in a particular cell may be used to direct SynMuv expression. Such enhancers include, without limitation, those enhancers which are characterized as tissue or cell specific in their expression.

Alternatively, if a SynMuv genomic clone is utilized as a therapeutic construct (for example, following its isolation by hybridization with the SynMuv cDNA described above), SynMuv expression is regulated by its cognate regulatory sequences or, if desired, by regulatory sequences derived from a heterologous source, e.g., any of the promoters or regulatory elements described above.

Less preferably, SynMuv gene therapy is accomplished by direct administration of the SynMuv mRNA to a cell predicted to undergo excess or insufficient cell proliferation. This mRNA may be produced and isolated by any standard technique, but is most readily produced by in vitro transcription using a SynMuv cDNA under the control of a high efficiency promoter (e.g., the T7 promoter). Administration of SynMuv mRNA to malignant cells is carried out by any of the methods for direct nucleic acid administration described above.

Ideally, the production of SynMuv protein by any gene therapy approach described above results in a cellular level of SynMuv that is at least equivalent to the normal, cellular level of SynMuv in an unaffected individual. Treatment by any SynMuv-mediated gene therapy approach may be combined with more traditional therapies.

Another therapeutic approach included within the invention involves direct administration of recombinant SynMuv protein, either to the site of a predicted or desirable cell proliferation event (for example, by injection) or systemically by any conventional recombinant protein administration technique. The actual dosage of SynMuv depends on a number of factors, including the size and health of the individual patient, but, generally, between 0.1 mg and 100 mg inclusive are administered per day to an adult in any pharmaceutically-acceptable formulation.

XIV. Administration of SynMuv Polypeptides. SynMuv Genes, or Modulators of SynMuv synthesis or Function A SynMuv protein, gene, or modulator may be administered with a pharmaceutically-acceptable diluent, carrier, or excipient, in unit dosage form. Conventional pharmaceutical practice may be employed to provide suitable formulations or compositions to administer SynMuv to patients suffering from or presymptomatic for a SynMuv-associated carcinoma. Any appropriate route of administration may be employed, for example, parenteral, intravenous, subcutaneous, intramuscular, intracranial, intraorbital, ophthalmic, intraventricular, intracapsular, intraspinal, intracisternal, intraperitoneal, intranasal, aerosol, or oral administration. Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found in, for example, "Remington's Pharmaceutical Sciences." Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for SynMuv modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

If desired, treatment with a SynMuv protein, gene, or modulatory compound may be combined with more traditional therapies for the disease such as surgery, radiation, or chemotherapy for cancers.

XV. Detection of A Condition Involving Altered Cell Proliferation

SynMuv polypeptides and nucleic acid sequences find diagnostic use in the detection or monitoring of conditions involving aberrant levels of cell proliferation. A decrease or increase in the level of SynMuv production may provide an indication of a deleterious condition. Levels of SynMuv expression may be assayed by any standard technique. For example, its expression in a biological sample (e.g., a biopsy) may be monitored by standard Northern blot analysis or may be aided by PCR (see, e.g., Ausubel et al., supra; *PCR Technology: Principles and Applications for DNA Amplification*, ed., H. A. Ehrlich, Stockton Press, NY; and Yap and McGee, Nucl. Acids. Res. 19:4294, 1991).

Alternatively, a patient sample may be analyzed for one or more mutations in the SynMuv sequences using a mismatch detection approach. Generally, these techniques involve PCR amplification of nucleic acid from the patient sample, followed by identification of the mutation (i.e., mismatch) by either altered hybridization, aberrant electrophoretic gel migration, binding or cleavage mediated by mismatch binding proteins, or direct nucleic acid sequencing. Any of these techniques may be used to facilitate mutant SynMuv detection, and each is well known in the art; examples of particular techniques are described, without limitation, in Orita et al., Proc. Natl. Acad. Sci. USA 86:2766–2770, (1989); and Sheffield et al., Proc. Natl. Acad. Sci. USA 86:232–236, (1989).

In yet another approach, immunoassays are used to detect or monitor SynMuv protein in a biological sample. SynMuv-specific polyclonal or monoclonal antibodies (produced as described above) may be used in any standard immunoassay format (e.g., ELISA, Western blot, or RIA assay) to measure SynMuv polypeptide levels; again comparison is to wild-type SynMuv levels, and a decrease in SynMuv production is indicative of a condition involving altered cell proliferation. Examples of immunoassays are described, e.g., in Ausubel et al., supra. Immunohistochemical techniques may also be utilized for SynMuv detection. For example, a tissue sample may be obtained from a patient, and a section stained for the presence of SynMuv using an anti-SynMuv antibody and any standard detection system (e.g., one which includes a secondary antibody conjugated to horseradish peroxidase). General guidance regarding such techniques can be found in, e.g., Bancroft and Stevens (*Theory and Practice of Histological Techniques*, Churchill Livingstone, 1982) and Ausubel et al. (supra).

In one preferred example, a combined diagnostic method may be employed that begins with an evaluation of SynMuv protein production (for example, by immunological techniques or the protein truncation test (Hogerrorst, F. B. L., et al., Nature Genetics 10:208–212 (1995) and also includes a nucleic acid-based detection technique designed to identify more subtle SynMuv mutations (for example, point mutations). As described above, a number of mismatch detection assays are available to those skilled in the art, and any preferred technique may be used (see above). By this approach, mutations in SynMuv may be detected that either result in loss of SynMuv expression or loss of SynMuv biological activity.

Mismatch detection assays also provide the opportunity to diagnose a SynMuv-mediated predisposition to diseases of cell proliferation. For example, a patient heterozygous for a SynMuv mutation may show no clinical symptoms and yet possess a higher than normal probability of developing one or more types of diseases. Given this diagnosis, a patient may take precautions to minimize their exposure to adverse environmental factors (for example, UV exposure or chemical mutagens) and to carefully monitor their medical condition (for example, through frequent physical examinations). This type of SynMuv diagnostic approach may also be used to detect SynMuv mutations in prenatal screens.

The SynMuv diagnostic assays described above may be carried out using any biological sample (for example, any biopsy sample or bodily fluid or tissue) in which SynMuv is normally expressed. Identification of a mutant SynMuv gene may also be assayed using these sources for test samples. Alternatively, a SynMuv mutation, particularly as part of a diagnosis for predisposition to SynMuv-associated proliferative disease, may be tested using a DNA sample from any cell, for example, by mismatch detection techniques; preferably, the DNA sample is subjected to PCR amplification prior to analysis.

Other Embodiments

In other embodiments, the invention includes any protein which is substantially identical to a mammalia SynMuv polypeptides (FIG. 2, 4, 6, 8, 9, 11, 13, or encoded by a nucleic acid of FIG. 26 or 27; such homologs include other substantially pure naturally-occurring mammalian SynMuv proteins as well as allelic variants; natural mutants; induced mutants; DNA sequences which encode proteins and also hybridize to the SynMuv DNA sequences of (FIG. 3, 5, 7, 8, 10, 12, 14, 26, or 27, under high stringency conditions or, less preferably, under low stringency conditions (e.g., washing at 2×SSC at 40° C. with a probe length of at least 40 nucleotides); and proteins specifically bound by antisera directed to a SynMuv polypeptide. The term also includes chimeric polypeptides that include a SynMuv portion.

The invention further includes analogs of any naturally-occurring SynMuv polypeptide. Analogs can differ from the naturally-occurring SynMuv protein by amino acid sequence differences, by post-translational modifications, or by both. Analogs of the invention will generally exhibit at least 85%, more preferably 90%, and most preferably 95% or even 99% identity with all or part of a naturally-occurring SynMuv amino acid sequence. The length of sequence comparison is at least 15 amino acid residues, preferably at least 25 amino acid residues, and more preferably more than 35 amino acid residues. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring SynMuv polypeptide by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, *Molecular Cloning: A Laboratory Manual* (2d ed.), CSH Press, 1989, or Ausubel et al., supra). Also included are cyclized peptides, molecules, and analogs which contain residues other than L-amino acids, e.g., D-amino acids or non-naturally occurring or synthetic amino acids, e.g., β or γ amino acids.

In addition to full-length polypeptides, the invention also includes SynMuv polypeptide fragments. As used herein, the term "fragment," means at least 20 contiguous amino acids, preferably at least 30 contiguous amino acids, more preferably at least 50 contiguous amino acids, and most preferably at least 60 to 80 or more contiguous amino acids. Fragments of SynMuv polypeptides can be generated by methods known to those skilled in the art or may result from normal protein processing (e.g., removal of amino acids from the nascent polypeptide that are not required for biological activity or removal of amino acids by alternative mRNA splicing or alternative protein processing events).

Preferable fragments or analogs according to the invention are those which facilitate specific detection of a Syn-Muv nucleic acid or amino acid sequence in a sample to be diagnosed.

All publications and patent applications mentioned in this specification are herein incorporated by reference to the same extent as if each independent publication or patent application was specifically and individually indicated to be incorporated by reference.

What is claimed is:

1. A substantially pure nucleic acid encoding a lineage-37 (LIN-37) polypeptide that is free of the genes which, in the naturally-occurring genome of the organism, flank the gene, said polypeptide having at least 95% amino acid sequence identity to SEQ ID NO: 1, wherein said polypeptide is hydrophilic, acts non-cell autonomously, and inhibits cell proliferation.

2. The nucleic acid of claim 1, wherein said nucleic acid is cDNA.

3. The nucleic acid of claim 1, wherein said nucleic acid is C.elegans DNA.

4. The nucleic acid of claim 1, wherein said nucleic acid is human DNA.

5. A substantially pure DNA encoding the amino acid sequence of SEQ ID NO: 1 that is free of the genes which, in the naturally-occurring genome of the organism, flank the gene, wherein said DNA encodes a polypeptide that is hydrophilic, acts non-cell autonomously, and inhibits cell proliferation.

6. A substantially pure synMuv nucleic acid comprising nucleic acid having at least 95% nucleotide sequence identity to the DNA sequence of SEQ ID NO:2, wherein said nucleic acid encodes a polypeptide that is hydrophilic, acts non-cell autonomously, and inhibits cell proliferation.

7. The nucleic acid of claim 1, wherein said DNA is operably linked to regulatory sequences for expression of said polypeptide and wherein said regulatory sequences comprise a promoter.

8. The nucleic acid of claim 7, wherein said promoter is a constitutive promoter.

9. The nucleic acid of claim 7, wherein said promoter is inducible by one or more external agents.

10. The nucleic acid of claim 7, wherein said promoter is cell-type specific.

11. A vector comprising the nucleic acid of claim 1, said vector being capable of directing expression of the peptide encoded by said DNA in a vector-containing cell.

12. An isolated cell which contains a substantially pure nucleic acid encoding a lineage-37 (LIN-37) polypeptide that is free of the genes which, in the naturally-occurring genome of the organism, flank the gene, said polypeptide having at least 95% amino acid sequence identity to SEQ ID NO: 1, wherein said polypeptide is hydrophilic, acts non-cell autonomously, and inhibits cell proliferation.

13. An isolated transgenic cell which contains a substantially pure nucleic acid encoding a lineage-37 (LIN-37) polypeptide having at least 95% amino acid sequence identity to SEQ ID NO: 1, wherein said polypeptide is hydrophilic, acts non-cell autonomously, and inhibits cell proliferation.

14. A substantially pure lineage-37 (lin-37) nucleic acid having at least 95% or greater nucleotide sequence identity to SEQ ID NO: 2 isolated according to the method comprising:
   (a) providing a cell sample;
   (b) introducing by transformation into said cell sample a candidate lin-37 nucleic acid;
   (c) expressing said candidate lin-37 nucleic acid within said cell sample; and
   (d) determining whether said cell sample exhibits a decrease in a cell proliferation response, whereby a decrease in cell proliferation identifies a lin-37 nucleic acid.

15. A substantially pure, naturally-occurring nucleic acid encoding a lineage-37 (LIN-37) polypeptide that is free of the genes which, in the naturally-occurring genome of the organism, flank the gene, said polypeptide having at least 95% amino acid sequence identity to the amino acid sequence of SEQ ID NO: 1, wherein said polypeptide is hydrophilic, acts non-cell autonomously, and inhibits cell proliferation.

16. The nucleic acid of claim 1, wherein said nucleic acid encodes a LIN-37 polypeptide that has 99% or greater amino acid sequence identity to the amino acid sequence of SEQ ID NO:1.

17. The nucleic acid of claim 1, wherein said nucleic acid encodes a LIN-37 polypeptide that has the ability to decrease cell proliferation by 50%.

18. The nucleic acid of claim 17, wherein said nucleic acid encodes a LIN-37 polypeptide that has the ability to decrease cell proliferation by one-fold.

19. A substantially pure, naturally-occurring synMuv nucleic acid comprising nucleic acid having at least 95% or greater nucleotide sequence identity to the nucleotide sequence of SEQ ID NO: 2, wherein said nucleic acid encodes a polypeptide that is hydrophilic, acts non-cell autonomously, and inhibits cell proliferation.

20. The synMuv nucleic acid of claim 6, wherein said synMuv nucleic acid comprises a nucleic acid sequence that has 99% or greater nucleotide sequence identity to the nucleotide sequence of SEQ ID NO:2.

21. The synMuv nucleic acid of claim 6, wherein said synMuv nucleic acid encodes a polypeptide that has the ability to decrease cell proliferation by 50%.

22. The synMuv nucleic acid of claim 21, wherein said synMuv nucleic acid encodes a polypeptide that has the ability to decrease cell proliferation by one-fold.

23. An isolated cell which contains a substantially pure naturally occurring nucleic acid encoding a lineage-37 (LIN-37) polypeptide that is free of the genes which, in the naturally-occurring genome of the organism, flank the gene, said polypeptide having at least 95% or greater amino acid sequence identity to SEQ ID NO: 1, wherein said polypeptide is hydrophilic, acts non-cell autonomously, and inhibits cell proliferation.

24. The isolated cell of claim 12, wherein said nucleic acid encodes a LIN-37 polypeptide that has 99% or greater amino acid sequence identity to the amino acid sequence of SEQ ID NO: 1.

25. The isolated cell of claim 12, wherein said nucleic acid encodes a LIN-37 polypeptide that has the ability to decrease cell proliferation by 50%.

26. The isolated cell of claim 25, wherein said nucleic acid encodes a LIN-37 polypeptide that has the ability to decrease cell proliferation by one-fold.

27. An isolated transgenic cell which contains a substantially pure naturally-occurring nucleic acid encoding a lineage-37 (LIN-37) polypeptide having at least 95% or greater amino acid sequence identity to SEQ ID NO: 1, wherein said polypeptide is hydrophilic, acts non-cell autonomously, and inhibits cell proliferation.

28. The isolated transgenic cell of claim 13, wherein said nucleic acid encodes a LIN-37 polypeptide that has 99% or greater amino acid sequence identity to the amino acid sequence of SEQ ID NO: 1.

29. The isolated transgenic cell of claim 13, wherein said nucleic acid encodes a LIN-37 polypeptide that has the ability to decrease cell proliferation by 50%.

30. The isolated transgenic cell of claim 29, wherein said nucleic acid encodes a LIN-37 polypeptide that has the ability to decrease cell proliferation by one-fold.

31. A substantially pure, naturally-occurring lineage-37 (lin-37) nucleic acid having at least 95% or greater nucleotide sequence identity to SEQ ID NO: 2 isolated according to the method comprising:
   (a) providing a cell sample;
   (b) introducing by transformation into said cell sample a candidate lin-37 nucleic acid;
   (c) expressing said candidate lin-37 nucleic acid within said cell sample; and
   (d) determining whether said cell sample exhibits a decrease in a cell proliferation response, whereby a decreased level of cell proliferation identifies a lin-37 nucleic acid.

32. The lin-37 nucleic acid of claim 14, wherein said lin-37 nucleic acid has 95% or greater nucleotide sequence identity to the nucleotide sequence of SEQ ID NO: 2.

33. A substantially pure, naturally-occurring lineage-37 (lin-37) nucleic acid having about 95% or greater nucleotide sequence identity to SEQ ID NO: 2 isolated according to the method comprising:
   (a) providing a cell sample;
   (b) introducing by transformation into said cell sample a candidate lin-37 nucleic acid;
   (c) expressing said candidate lin-37 nucleic acid within said cell sample; and
   (d) determining whether said cell sample exhibits a decreased cell proliferation response, whereby a decreased level of cell proliferation identifies a lin-37 nucleic acid.

34. The lin-37 nucleic acid of claim 33, wherein said lin-37 nucleic acid has the ability to decrease cell proliferation by 50%.

35. The lin-37 nucleic acid of claim 34, wherein said lin-37 nucleic acid has the ability to decrease cell proliferation by one fold.

* * * * *

SEQUENCE LISTING

```
<160> NUMBER OF SEQ ID NOS: 18

<210> SEQ ID NO 1
<211> LENGTH: 275
<212> TYPE: PRT
<213> ORGANISM: Caenorhabditis elegans

<400> SEQUENCE: 1

Met Ser Glu Ile Asp Pro Leu Ala Glu Phe Leu Leu Pro Glu Asp Gly
  1               5                  10                  15

Asp Arg Asn Ala Arg Gln Asn Asp Pro Leu Ile Ser Gly Gly Pro Leu
             20                  25                  30

Pro Leu Glu Ser Pro Ser Arg Lys Leu Thr Ser Leu Leu Ser Tyr Asp
         35                  40                  45

Pro Thr Val Pro Glu Ser Pro Asp Met Lys Phe Ala Arg Lys Arg Leu
     50                  55                  60

Gly Asn Leu Leu Thr Thr Ile Lys His His Pro Ser Glu Ile Ile Gly
 65                  70                  75                  80

Val Leu Pro Glu Asp Tyr Thr Arg Ala Asp Glu Glu Pro Gly Arg Gln
             85                  90                  95

Gly Arg Pro Pro Gly Arg Pro Arg Lys Met Pro Arg His Glu Ser Ser
            100                 105                 110

Thr Ser Leu Met Glu Ser Pro Arg Lys Thr Met Thr Arg Asp Ser Lys
        115                 120                 125

Ile Met Phe Glu Leu Arg Gly Lys Pro Phe Glu Met Ile Ala Gly Arg
    130                 135                 140

Phe Glu Glu Glu Tyr Ser Leu Gly Arg Ala Trp Val Lys Gly His Met
145                 150                 155                 160

Asn Asn Glu Tyr Glu Pro Ile Lys Ala Gln Arg Thr Asp Tyr Ala Pro
                165                 170                 175

Asn Leu Ala Val Asp Tyr Leu Ala Cys Arg Glu Ile His Arg Met Pro
            180                 185                 190

Arg Pro Asp Lys Ser Ile Pro Glu Leu Pro Ile Val Pro Ser Arg Ile
        195                 200                 205

Asp Glu Phe Asp Ala Thr Val Asp Pro Arg Tyr Glu Thr Asp Leu Lys
    210                 215                 220

Asn Glu Tyr Ile Arg His Trp Lys Gln Val Lys Lys Gly Trp Cys Ala
225                 230                 235                 240

His Gln Arg Arg Arg Thr Ala Pro His Ala Arg Ser Ile Ala Leu Ile
                245                 250                 255
```

Asn Lys Ile Tyr Gln Pro Gly Glu Ser Lys Thr Val Glu Gln Ala Leu
            260                 265                 270
Gly Leu Ile
        275

<210> SEQ ID NO 2
<211> LENGTH: 954
<212> TYPE: DNA
<213> ORGANISM: Caenorhabditis elegans

<400> SEQUENCE: 2
atgtcagaaa tagatccact tgccgagttc ttgcttccag aagacggaga tcgaaatgct     60
cgtcaaaatg atccattgat aagcggaggt ccacttccat ggaatcgcc aagcagaaaa    120
ctcacatccc tgttatccta tgatccgaca gttccggagt caccggatat gaaattcgcc    180
agaaaacgtc tgggaaatct gctgacaacc ataaacatc acccatcgga ataattgga    240
gtactcccag aagattatac tcgtgctgat gaagagcccg gcgccaagg acgtccacca    300
ggtcgccctc gtaagatgcc gcgtcacgaa tcttcaactt cacttatgga atcaccacgc    360
aagactatga ctcgtgattc taaaattatg tttgaattgc gtggaaaacc attcgaaatg    420
atagctggac gttttgaaga agaatattca cttggtagag catgggttaa aggacacatg    480
aataatgaat atgaaccaat aaaagctcaa aggacagact atgcaccgaa tctggctgtt    540
gattatcttg catgtcgcga gattcatcga atgccacgtc agataaatc aattcctgag    600
ctgccaattg ttccatctag aatcgatgaa ttcgacgcta cagtcgatcc aagatatgaa    660
acagatttga aaaatgaata cattcgtcat tggaaacaag tcaaaaaagg ttggtgtgct    720
catcaacgtc gtcggactgc tccccatgca agaagcatag cattaatcaa caaaatctac    780
cagcctggag agtcgaaaac tgtcgagcaa gcacttggtc ttatttaaat attctaacat    840
gtaatttcaa tttatctctt actttctgat cttgctatca catgtctctt atttcaaaaa    900
tctcacttta aaattcatat aaataatggg tttattcaaa tacatcatct tgac          954

<210> SEQ ID NO 3
<211> LENGTH: 961
<212> TYPE: PRT
<213> ORGANISM: Caenorhabditis elegans

<400> SEQUENCE: 3

Met Pro Lys Arg Ala Ala Asp Glu Pro Gly Thr Ser Thr Thr Asp Pro
 1               5                  10                  15
Phe His Glu Gln Ser Pro Phe Asp Ala Val Leu Ala Gly Thr Glu Thr
            20                  25                  30
Thr Asp Thr Ile Cys Glu Glu Pro Ala Lys Arg Ile Asp Leu Asp
        35                  40                  45
Ile Lys Gln Glu Phe Asn Gly Gly Val Gln Ser Gly Gly Leu Ile Lys
    50                  55                  60
Asn Glu Ser Glu Leu Thr Gln Met Thr Ile Lys Gln Glu Thr Glu Gly
65                  70                  75                  80
Asn Ile Asn Glu Ala Arg Arg Glu Glu Asp Glu Gln Asp Glu
                85                  90                  95
Asp Ser Arg Thr Ser Met Pro Pro Ala Leu Gly Glu Asp Asp Tyr
            100                 105                 110
Glu Glu Asp Asp Ala Asp Ser Phe Ile Asp Lys Thr Asn Thr Pro Pro
        115                 120                 125
Pro Ser Gln Ser Phe Leu Glu Gly Cys Arg Ala Ala Asn Leu Pro Asn

-continued

```
            130                 135                 140
Asp Ile Val Thr Gly Ala Trp Glu Thr Tyr Asn His Ala Val Gln Arg
145                 150                 155                 160
Val Ser Leu Glu Gly Ser Glu Ser Ala Trp Gln Leu Ser Ala Ile Tyr
                165                 170                 175
Tyr Tyr Leu Leu Ser Lys Gly Ile Lys Arg Gly Lys Thr Ile Arg
                180                 185                 190
Ile Leu Ile Gln Pro Phe Pro Val Ser Ile Leu Thr Ile Ala Asn Ser
                195                 200                 205
Phe Asp Ile Ser Val Ala Glu Met Leu Asp Lys Thr Ala Arg Phe Val
210                 215                 220
Glu Ile Ile His Ser Arg Lys Ile Arg Arg Tyr Gln Glu Tyr Ile Arg
225                 230                 235                 240
Arg Ile Gln Glu Gly Leu Ala Val Ser Cys Val Ile Phe Lys Lys Phe
                245                 250                 255
Cys Arg Ile Phe Cys Lys Ile Phe Glu Glu Ile Lys Val Gly Ser Glu
                260                 265                 270
Asn Cys Pro Ser Ser His Glu Leu Phe Thr Val Leu Trp Thr Ser Phe
                275                 280                 285
Leu Val Met Lys Ser Arg Met Thr Val Asp Asp Leu Ile Ser Asn Tyr
                290                 295                 300
Gln Leu Leu Phe Ser Ile Leu Asp Gln Val Tyr Thr Glu Met Cys Ser
305                 310                 315                 320
Met Lys Glu Gly Ile Val His His Leu Asn Gln Lys Phe Val Glu Asp
                325                 330                 335
Leu Leu Glu Asn Asp Cys Thr Ile Ile Arg Ala Leu Cys Thr Gln Phe
                340                 345                 350
Gly Gly Ser Val Leu Asp Ala Arg His Phe Ser Asp His Thr Phe Lys
                355                 360                 365
Lys Met Glu Lys Thr Gly Ile Pro Ser Thr Trp Asn Phe Gln Glu Phe
                370                 375                 380
Arg Asp Leu Ile Met Asn Val Pro Lys Thr Ala Tyr Glu Asn Tyr Leu
385                 390                 395                 400
Leu Gln Arg Gly Ser Ile Asp Glu Arg Ile Phe Ile Pro Ser Val Glu
                405                 410                 415
Asp Phe Ser Lys Ile Phe Gln Ser Pro Asp Thr Tyr Ser Val Ala Asp
                420                 425                 430
Ile Leu Lys Val Ser Tyr Ser Gly Arg Arg Phe Arg Asp Ala Glu Phe
                435                 440                 445
Leu Thr Lys Ile Ser Asn Asn His Cys Leu Glu Lys Leu Ala Leu Gly
                450                 455                 460
Gly Lys Val Ala Ser Glu Lys Leu Val Thr Gln Ser Lys Glu Gln Pro
465                 470                 475                 480
Arg Val Pro Cys Val Glu Tyr Asn Leu Glu Leu Gly Asn Tyr Pro Asp
                485                 490                 495
Asp Leu Glu Ser Asn Asn Gln Ser Leu Tyr Asn Arg Leu Thr Lys Ile
                500                 505                 510
Ile Gly Ser Trp Lys Leu Glu Asn Ser Lys Leu Glu Glu Val Cys Gly
                515                 520                 525
Thr Met Ser Asp Ser Pro Met Ala Thr Ile Leu Leu Lys Ser Asp Glu
                530                 535                 540
Met Thr Asn Lys Phe Glu Arg Thr Leu Ser Ala Glu Leu Gly Glu Thr
545                 550                 555                 560
```

-continued

```
Ile Asn Glu Asn Ile Pro Lys Tyr His Tyr Asn Val Arg Lys Glu Leu
                565                 570                 575
Glu Leu Val Phe Leu Ile Phe Met Glu Lys Ile Ile Val Ala Glu Leu
            580                 585                 590
Lys Lys Lys Val Arg Glu Glu Asp Leu Leu Asn Val Ile Arg Arg Glu
        595                 600                 605
Glu Phe Leu Asp Ser Val Phe Cys Phe Val Glu Leu Ile Leu Val
    610                 615                 620
Ser Asn Gly Tyr Asp Arg Pro Phe Pro Trp Ser Ala Glu Leu Cys Gly
625                 630                 635                 640
Val His Pro Phe Met Phe His Lys Val Ile Asp Leu Met Ile Thr His
                645                 650                 655
Glu Lys Gln Leu Ser Arg Gln Met Val Gln His Phe Ser Arg Ile Glu
                660                 665                 670
Glu Thr Val Ile Glu Tyr Phe Ser Trp Lys Ser Asp Ser Pro Leu Trp
            675                 680                 685
Pro Met Val Val Arg Cys Pro Phe Ala His Phe Gln Glu Phe Gly Glu
        690                 695                 700
Asp Trp Ala Asp Lys Leu Asn Ser Tyr Ser Pro Ile Lys Phe Thr Pro
705                 710                 715                 720
Ile Lys Lys Pro Asp Asp Leu Arg Asp Glu Leu Gly Arg Pro Ile Val
                725                 730                 735
Pro Gln Asn Gln Thr Ser Arg Thr Leu Arg Ile Phe Leu Lys Arg Thr
                740                 745                 750
Tyr Phe Thr Ala Ala Arg Arg Leu Gln Asp Leu Thr Asp Arg Val Ser
            755                 760                 765
Met Gly Ala Arg Ala Lys Ser Gln Cys Trp Ser Leu Phe Asp Tyr Leu
        770                 775                 780
Leu Arg Asn Asp Thr Leu Ile Phe Met Asp Arg His Leu Asp Gln Ile
785                 790                 795                 800
Leu Leu Cys Cys Val Phe Val Ile Met Lys Ile Asn Glu Ser Ser Met
                805                 810                 815
Leu Phe Thr Glu Ile Met Ala Gln Tyr Arg Arg Gln Ser Ala Asn Ser
                820                 825                 830
Leu Leu Val Tyr Arg Ser Val Thr Val Phe Gln Glu Gln Leu Asn Pro
            835                 840                 845
Glu Asn Pro Gln Ala Val Asn Thr Lys Glu Thr Ile Leu Glu Arg Leu
        850                 855                 860
Glu Gly Pro Gln Lys Glu Lys Thr Thr Val Asp Ile Ile Lys Tyr Tyr
865                 870                 875                 880
Asn Ile Glu Phe Arg Asp Arg Ile Lys Tyr Ile Ile Gly Gln Ile Asp
                885                 890                 895
Ser Ala Ser Asp Glu Asp Leu Met Glu Met Pro Val Ala Thr Glu Ser
                900                 905                 910
Gly Leu Met Pro Val Arg Val Tyr Leu Thr His Lys Leu Ser Ile Gln
            915                 920                 925
Thr Leu Pro Lys Thr Lys His Gly Glu Ser Lys Gln Glu Arg Ala Ile
        930                 935                 940
Ala Asn Leu Glu Lys Ser Gly Ile Thr Ile Ala Met Glu Arg Ser Gly
945                 950                 955                 960
Asp
```

<210> SEQ ID NO 4
<211> LENGTH: 3209
<212> TYPE: DNA
<213> ORGANISM: Caenorhabditis elegans

<400> SEQUENCE: 4

| | | | | | |
|---|---|---|---|---|---|
| atgccgaaac | gagcagccga | tgagcctgga | acatcaacaa | ctgacccatt | tcacgagcaa | 60 |
| agcccattcg | atgccgtgtt | agccggcacg | gagacaacgg | atacaatatg | tgaagagcca | 120 |
| ccagcaaaac | gaatcgactt | agatataaag | caagaattca | atggtggagt | gcaaagtgga | 180 |
| gggctgatta | aaaatgaatc | cgaattgact | caaatgacaa | tcaaacaaga | aacagaagga | 240 |
| aacataaatg | aagctagacg | agaagaagaa | gacgaagaac | aagatgaaga | ttccagaaca | 300 |
| tcaatgccac | ctgcattggg | agaagatgat | gattatgagg | aggatgatgc | tgatagtttt | 360 |
| attgataaaa | ctaatacacc | gccaccatca | caatcatttc | tggaaggatg | tcgagcagct | 420 |
| aatttaccaa | atgacattgt | tactggtgca | tgggaaacgt | acaaccacgc | ggttcaacgg | 480 |
| gtttctcttg | agggttcgga | atcggcgtgg | caactatcag | caatttacta | ttatcttcta | 540 |
| tcaaaggaa | taaacgtcg | tggaaaaaca | atccgtattc | tcattcaacc | gtttcctgtt | 600 |
| tcgatactta | caattgccaa | ctcatttgac | atatccgttg | ctgaaatgct | tgacaaaact | 660 |
| gctcgatttg | tggaaattat | acattccaga | aaaattcgtc | gttatcaaga | atatattcga | 720 |
| cgaattcaag | aaggactcgc | agtttcttgt | gtgatattca | aaaagttttg | ccgaattttc | 780 |
| tgcaaaatat | tcgaggagat | caaagttgga | tccgaaaatt | gtccatcttc | tcatgaactt | 840 |
| tttacggttc | tttggacatc | ttttctggtg | atgaaaagtc | gaatgacagt | ggacgatttg | 900 |
| atttcaaatt | atcaacttct | ttttcaata | cttgatcaag | tatataccga | aatgtgttca | 960 |
| atgaaagagg | gaatagttca | tcatttgaat | caaaaatttg | ttgaagatct | tcttgaaaat | 1020 |
| gattgtacga | ttattcgagc | tctttgcaca | caatttggtg | aagtgttct | tgatgcacgg | 1080 |
| cacttttctg | atcatacttt | taagaaaatg | gagaagactg | gaattccgtc | cacttggaat | 1140 |
| tttcaagagt | ttcgagattt | gatcatgaac | gttccaaaaa | cggcatatga | gaattatcta | 1200 |
| ttgcaacgtg | gaagtattga | tgagcggatt | ttcattccaa | gcgttgagga | cttttcaaaa | 1260 |
| atttttccaat | ccccggacac | atactcagta | gcagatattc | tcaaagtgtc | ttactctgga | 1320 |
| agacgttttcc | gtgatgcaga | atttcttaca | aaaatctcaa | ataatcattg | tctgaaaaag | 1380 |
| ttggcattag | gtggaaaagt | agcatcagaa | aagttggtaa | cacagtcaaa | agaacagccg | 1440 |
| agagttccgt | gtgttgagta | taatctcgaa | ttgggaaatt | atccagacga | tttgaatcg | 1500 |
| aacaatcaaa | gtctttataa | tagattgaca | aaaattattg | gaagctggaa | attggagaat | 1560 |
| tcgaaactcg | aagaagtgtg | tggcacaatg | tccgacagtc | caatggcaac | aattcttctg | 1620 |
| aaaagtgatg | aaatgacaaa | taaattcgag | cgaactttat | ctgcagaact | cggagagacg | 1680 |
| atcaatgaga | atattcctaa | atatcactat | aatgttcgaa | agaattgga | attagtttt | 1740 |
| ctcatttca | tggagaaaat | aattgttgca | gaattgaaaa | agaaagtacg | agaggaggac | 1800 |
| ttgctgaatg | tgattcgtcg | ggaagaattt | cttgattcag | ttttctgttt | ctgtgttgaa | 1860 |
| ctgatccttg | tttccaatgg | atatgatcgt | ccatttccat | ggagtgctga | actgtgtgga | 1920 |
| gtacatccat | ttatgtttca | taagtaatt | gatttgatga | taacacatga | gaaacagcta | 1980 |
| agtcgtcaaa | tggttcaaca | ttttagtcga | attgaagaaa | ctgtaattga | gtattttcg | 2040 |
| tggaagtctg | atagtccatt | atggccaatg | gttgtcaggt | gtccatttgc | acatttcaa | 2100 |
| gaattcggag | aggattgggc | tgataaatta | aactcgtact | caccaataaa | attcactcca | 2160 |

-continued

```
atcaagaagc ctgatgatct acgagacgaa cttggaagac ctatagttcc tcaaaatcaa    2220
acttcaagaa ctctaagaat ttttttgaaa agaacttatt tcaccgccgc tcgtcgactt    2280
caagatctca ctgatcgtgt ttcaatggga gctcgtgcaa atcacaatg ctggtcactt     2340 ttcgattatc ttcttcgcaa tgacactttg attttatgg atagacatct tgatcaaatt    2400
cttctttgtt gcgtgtttgt cattatgaag ataaatgagt catcaatgct tttcacggaa    2460
ataatggctc aatatcgacg acaatcagcc aattctttgc tggtctaccg aagtgttaca    2520
gtattccaag aacaactgaa tcccgaaaat ccacaggcag taaacacgaa ggagacaatt    2580
ttggaacgtc ttgaaggtcc acaaaagaa aaacgacag ttgatataat caaatattat      2640
aatatcgagt ttcgggatcg tatcaagtat attatcggtc aaattgatag tgcttcagat    2700
gaagatttga tggaaatgcc ggttgcaaca gaatctggat tgatgcctgt tcgagtttat    2760
ttaacacata aattatcgat tcaaacgctt ccaaaaacga acacggaga gtcgaaacaa     2820 gaaagagcta ttgcgaacct tgaaaaatct ggaattacga tcgctatgga acggtctgga    2880
gattaaaaat gattgttgtg aatactttga acttttaat gcattttga ttaatcattt      2940 agtacttctt ttctcgtcta tttttttatc ttttccttca aattcaggca agtaattata    3000
ctttccattt ctaattgatt gcttcaaaat agacgtctag ttatattcaa aacaatcccc    3060
cttttgaatt ggaatcttca aatatcgtat taaatattaa tattgtaatc attttcaca    3120 atcccccatg ccattattgt tactgatttt ttctctcttt ttaaccatca tcgataaatt    3180
cattttacag ttataaaaaa aaaaaaaaa                                       3209
```

<210> SEQ ID NO 5
<211> LENGTH: 417
<212> TYPE: PRT
<213> ORGANISM: Caenorhabditis elegans

<400> SEQUENCE: 5

```
Met Ala Thr Leu Glu Asp Gly Thr Ser Glu Asp Arg Val Ala Asn Asp
  1               5                  10                  15

Glu Tyr Lys Ile Trp Lys Lys Asn Thr Pro Phe Leu Tyr Asp Leu Val
             20                  25                  30

Met Thr His Ala Leu Glu Trp Pro Ser Leu Ser Val Gln Trp Leu Pro
         35                  40                  45

Asp Val Ala Lys Asp Asn Ser Asp His Thr Ile His Arg Leu Ile Leu
     50                  55                  60

Gly Thr His Thr Ser Asp Glu Gln Asn His Leu Leu Ile Ser Lys Ile
 65                  70                  75                  80

Cys Met Pro Thr Asp Asp Ala Gln Phe Asp Ala Ser Arg Tyr Asp Thr
             85                  90                  95

Glu Arg Ser Glu Tyr Gly Gly Phe Gly Ala Val Asn Gly Lys Val Glu
            100                 105                 110

Pro Asp Ile Arg Ile Asn His Glu Gly Glu Val Asn Arg Ala Arg Tyr
        115                 120                 125

Met Pro Gln Lys Ser Asn Ile Ile Ala Thr Lys Ser Pro His Ala Asp
    130                 135                 140

Val Tyr Ile Phe Asp Tyr Leu Lys His Ser Ala Val Pro Arg Asp Asn
145                 150                 155                 160

Thr Phe Asn Pro Leu Ile Arg Leu Lys Gly His Thr Lys Glu Gly Tyr
                165                 170                 175

Gly Leu Ser Trp Asn Pro Asn Lys Glu Gly Leu Ile Leu Ser Ala Ser
            180                 185                 190
```

```
Asp Asp Gln Thr Val Cys His Trp Asp Ile Asn Ala Asn Gln Asn Val
            195                 200                 205

Ala Gly Glu Leu Gln Ala Lys Asp Val Phe Lys Gly His Glu Ser Val
            210                 215                 220

Val Glu Asp Val Ala Trp His Val Leu His Asp Gly Val Phe Gly Ser
225                 230                 235                 240

Val Gly Asp Asp Lys Lys Leu Leu Ile Trp Asp Val Arg Thr Ser Thr
                245                 250                 255

Pro Gly His Cys Ile Asp Ala His Ser Ala Glu Val Asn Cys Leu Ala
            260                 265                 270

Phe Asn Pro Tyr Ser Glu Phe Ile Leu Ala Thr Gly Ser Ala Asp Lys
            275                 280                 285

Thr Val Ala Leu Trp Asp Leu Arg Asn Leu Arg Met Lys Leu His Ser
            290                 295                 300

Phe Glu Ser His Arg Asp Glu Ile Phe Gln Val Gln Trp Ser Pro His
305                 310                 315                 320

Asn Glu Thr Ile Leu Ala Ser Ser Gly Thr Asp Lys Arg Leu His Val
            325                 330                 335

Trp Asp Leu Ser Lys Ile Gly Glu Asp Gln Ser Ala Glu Asp Ala Glu
            340                 345                 350

Asp Gly Pro Pro Glu Leu Leu Phe Ile His Gly Gly His Thr Ala Lys
            355                 360                 365

Ile Ser Asp Phe Ser Trp Asn Pro Asn Glu Pro Trp Val Val Cys Ser
            370                 375                 380

Val Ser Glu Asp Asn Ile Leu Gln Val Trp Gln Met Ala Asp Asn Ile
385                 390                 395                 400

Tyr Asn Glu Val Asp Glu Glu Thr Pro Ala Asp Val Val Glu Arg Gln
                405                 410                 415

Gln

<210> SEQ ID NO 6
<211> LENGTH: 1462
<212> TYPE: DNA
<213> ORGANISM: Caenorhabditis elegans

<400> SEQUENCE: 6
atggccactc ttgaagatgg aacctccgaa gatcgcgtcg caaatgatga atacaaaatt      60
tggaaaaaga cacccccgtt cttgtacgat ctcgtaatga cacatgcgct tgagtggcct    120
tcactcagtg ttcaatggct cccagacgtt gcgaaggata cagcgacca tactattcat     180 cggctcattc ttgaaactca tacttcagat gagcagaatc acttgcttat ttctaagatc    240
tgtatgccaa cggatgatgc ccaatttgat gcatctcgct acgataccga gcgcagtgaa    300
tacggtggtt tcggagctgt taacggaaaa gtggaacccg atattcgcat taaccacgaa    360
ggggaggtta acagagctcg ttacatgcct caaaagtcga atatcattgc tacaaagtct    420
ccacatgctg atgtttacat tttcgactat ttaaagcact ctgctgttcc tcgtgataac    480
acgttcaatc cgcttatcag actgaaagga cacacgaagg aaggctatgg attatcatgg    540
aatccaaaca aagaaggttt gattctatca gcgtcagatg atcagacagt tgtcattgg    600 gatatcaacg caaatcagaa tgttgccggg gaattgcaag cgaaggatgt tttcaaaggt    660
cacgagtcag tcgttgaaga tgttgcttgg cacgttttgc atgatggtgt cttcggatcg    720
gttggtgacg ataagaaatt gctcatttgg gatgtgcgca aagcactccc tggacactgt    780
```

-continued

```
atcgatgctc attctgccga agttaactgt ctcgcattca atccatattc cgaattcatt      840
ctggccaccg gatcagctga taaaactgtc gctctttggg atctacgtaa tctacgaatg      900
aaacttcact catttgaatc acatcgtgat gaaatcttcc aagttcagtg gagtccacac      960
aacgagacta ttcttgcatc cagcggtact gataaacgtc ttcatgtgtg ggacctatct     1020
aagattggag aagaccaatc tgccgaagac gcggaagatg gtccaccaga gctgttgttt     1080
attcacggtg ggcacaccgc caagatcagc gatttctcgt ggaacccgaa cgagccttgg     1140
gttgtgtgca gtgtgtcaga agacaatatt ctccaagtgt ggcaaatggc tgataacata     1200
tacaacgaag ttgacgaaga aactccagcc gatgtggtag agagacaaca gtaaaatacg     1260
tgaaacgcgc ttaaattatt tgtatttaac ttctatcctt ctttaatttt gcatctcaac     1320
aaattgttca tcttaccatt tattcaaacg catattcttc accaactaag tttttaaagt     1380
taaaatgtta ccttgagata tgatcatatt ttgttgaacc tgaaataaat tcgatgacca     1440
ttgtcaaaaa aaaaaaaaaa aa                                              1462
```

<210> SEQ ID NO 7
<211> LENGTH: 575
<212> TYPE: PRT
<213> ORGANISM: Caenorhabditis elegans

<400> SEQUENCE: 7

```
Met Gly Arg Arg Ile Val Gln Met Pro Thr Gly Leu Pro Arg Ser Tyr
  1               5                  10                  15

Gln Asp Glu Ser His Asn Glu Pro Val Gly Trp Asp Glu Pro Ser Gly
             20                  25                  30

Val Gly Gly Ser Ser Gly Ala Gly Gly Gln Gln Ser Asp Lys Pro Thr
         35                  40                  45

Gly Leu Arg His Phe Ser Thr Lys Val Cys Glu Lys Val Lys Glu Lys
     50                  55                  60

Gly Leu Thr Asn Tyr Asn Glu Val Ala Asp Glu Leu Val Ala Asp Tyr
 65                  70                  75                  80

Phe Gln Asn Asn Leu Ile Lys Gln Ile Asp Val Val Lys Gln Glu Tyr
                 85                  90                  95

Asp Met Lys Asn Ile Arg Arg Val Tyr Asp Ala Leu Asn Val Leu
            100                 105                 110

Leu Ala Met Asn Ile Ile Thr Lys Ser Lys Lys Asp Ile Arg Trp Ile
        115                 120                 125

Gly Leu Pro Ala Ser Ala Ser Gln Glu Ile Ser Arg Leu Glu Glu Glu
    130                 135                 140

Lys Ser Arg Arg Glu Ala Ser Ile Ser Ser Lys Lys Gln Ala Leu Glu
145                 150                 155                 160

Glu Met Val Leu Gln Ile Val Ser Tyr Lys Asn Leu Val Glu Arg Asn
                165                 170                 175

Arg Lys Asn Glu His Lys Asn Gly Arg Pro Glu Asn Asp Thr Val Leu
            180                 185                 190

His Leu Pro Phe Leu Ile Ile Asn Thr Asp Lys Glu Ala Asn Val Glu
        195                 200                 205

Cys Ser Val Ser Ser Asp Lys Ser Glu Phe Leu Phe Ser Phe Asp Lys
    210                 215                 220

Lys Phe Glu Ile His Asp Asp Phe Glu Ile Leu Lys Lys Leu Asn Leu
225                 230                 235                 240

Ala Cys Ser Leu Glu Thr Thr Asn Pro Thr Ala Glu Glu Val Lys Thr
                245                 250                 255
```

```
Ala Lys Ser Phe Leu Pro Thr Leu His Gln His Tyr Val Asp Glu Ile
            260                 265                 270

Ile Ala Asn Arg Lys Val Glu Ala Glu Lys Glu Glu Lys Arg Lys
        275                 280                 285

Gln Gln Gln Leu Ile Ala Asp Gln Met Ser Met Asn Leu Ser Gln Ala
            290                 295                 300

Gln Tyr Val Glu Pro Thr Ser Ser Leu Ala Gln Met Ser Tyr Ser Ser
305                 310                 315                 320

Arg Phe Asn Arg Gln Leu Gln Glu His Leu Ile Asn Asp Gly Ser Glu
                325                 330                 335

Asp Arg Ser Ala Ala Ala Gly Ile Met Glu Arg Asp Tyr Asp Met Asp
            340                 345                 350

Lys Asn Val Asn Gln Gly Ser Ala Ser Arg Gly Pro Met Tyr Asn Thr
            355                 360                 365

Tyr Ser Pro Gln Lys Ile Arg Ala Gln Val Asn Thr Pro Leu Gln Val
    370                 375                 380

Pro Pro Val Thr Lys Arg Tyr Tyr Val Gln Lys Thr Gln Gly Pro Met
385                 390                 395                 400

Lys His Asp Met Thr Pro Val Val Arg Thr Val Asn Arg Pro Tyr Ser
                405                 410                 415

Thr Val Pro Pro Asp Arg Arg Leu Ser Thr Gly Ala Thr Ser Val Asn
            420                 425                 430

Ser Gly Pro Val Lys Tyr Tyr Val Pro Gln Gly His Gln Pro Met His
            435                 440                 445

Gln Pro Val Gly Gln Arg Tyr Arg Val Arg Pro Gln Gln Pro Gln Met
    450                 455                 460

Ser His Met Gly Gln Pro His Gln Val Gln Gln Arg Val Val Tyr Pro
465                 470                 475                 480

Ala Gly Ser Ile Ser Gly His Gln Leu Gln Pro Gly Gln Arg Ile Val
                485                 490                 495

Thr Gln Arg Ile Val Ala Pro Gly Gly Pro His Pro Pro Gly Thr Ile
            500                 505                 510

Val Arg Lys Val Ile Arg Lys Ile Val Val Asn Asn Pro Lys Gln Ser
            515                 520                 525

Pro Ala Gln Gln Val Ile Gln Lys Lys Met Met Glu Gln Asp Met Cys
    530                 535                 540

Thr Phe Glu Arg Lys Thr Glu Gln Pro Met Thr Ser Ala Gln Ala Ala
545                 550                 555                 560

Ala Leu Ile Gln His Pro Gln Pro Glu Glu Tyr Asp Tyr Phe Gln
                565                 570                 575
```

<210> SEQ ID NO 8
<211> LENGTH: 1832
<212> TYPE: DNA
<213> ORGANISM: Caenorhabditis elegans

<400> SEQUENCE: 8

```
aaaatcttga ttcgtccagg caggtcctgt agaaatgaac ccgacaaact acgatccccg    60
tatcggccaa ccggcacaaa gtcgaccaca agtataccct gagtatggga agacgaattg   120
ttcaaatgcc tacaggtctt cctcgttcat accaagatga gagtcacaat gaacctgtgg   180
gctgggatga accttcggga gttggaggat ctagtggagc aggaggtcaa caatctgaca   240
aaccaaccgg actcagacat ttttccacga agtttgtga aaaggtgaaa gaaaaaggat   300
```

-continued

```
tgacgaatta caatgaagtg gctgatgaac tggtagcaga ttactttcaa aataatctta      360
tcaagcagat tgatgttgtg aaacaagaat acgatatgaa aaatattcgg aggagagtat      420
acgatgcgtt gaacgttctt ttggcaatga atatcatcac aaaaagcaag aaagatatca      480
gatggattgg acttcctgct tcagcttcac aagaaatttc gagattggaa gagagaaat      540
cgcgacggga agccagcata agttccaaaa agcaggctct cgaagaaatg gtattgcaaa      600
ttgtttctta caaaaatttg gtcgaacgga atagaaaaaa tgagcacaaa aatggtcgcc      660
cagaaaacga cactgtactt catcttccgt ttttaataat taatactgat aaagaagcaa      720
atgtggaatg cagtgtatca tcagacaaat ccgaatttct gttctcgttc gacaagaagt      780
ttgaaattca cgatgattc gaaatttta aaagttgaa ccttgcatgc agtttggaga        840
ctacaaatcc cacagcggaa gaagtcaaaa ctgcgaaaag cttttttgcca accttacacc      900
agcactatgt cgacgaaatc attgccaacc gtaaaaaggt tgaagcagaa aagaggaaa      960
agagaaaaca caacagttg attgctgatc aaatgtctat gaacctctca caagcccaat    1020
acgttgagcc gacaagctct ttggcgcaaa tgtcatattc atcgcgattc aacagacagc    1080
ttcaggagca tttgataaac gatggaagtg aggacagaag tgctgctgcc ggtataatgg    1140
aacgcgatta tgatatggat aagaatgtta atcagggatc agccagccga gggccaatgt    1200
ataatactta tagtccacaa aagattcgag ctcaagttaa cacgcctctt caagtaccac    1260
ccgttaccaa acgatattac gtacagaaga cacaaggacc aatgaagcat gatatgactc    1320
ccgtcgttcg aactgtcaat cggccgtact ctactgtacc tccagatcgc aggctctcaa    1380
ctggagctac ttctgtgaat tcaggacctg taaaatacta cgtgccacaa ggacatcaac    1440
cgatgcatca gccagttggt cagagatata gagttcgtcc acagcaacca caaatgagtc    1500
atatgggtca gccacatcaa gtgcaacaga gagttgtcta tcctgctgga agcatttctg    1560
gacatcagtt acaacctgga caacgaatcg taactcagcg aattgttgct ccaggtggtc    1620
cacacccgcc gggcacaatt gttcggaaag tgattcgtaa aattgttgtc aacaatccaa    1680
agcaatctcc agctcaacaa gttatacaaa agaaaatgat ggagcaagat atgtgcacat    1740
ttgaacgcaa aacggaacag ccgatgactt ctgcgcaggc cgctgctctc attcaacacc    1800
ctcaaccgga ggaatacgat tatttccagt aa                                  1832
```

<210> SEQ ID NO 9
<211> LENGTH: 324
<212> TYPE: PRT
<213> ORGANISM: Caenorhabditis elegans
<400> SEQUENCE: 9

```
Met Glu Leu Gln Lys Ala Leu Glu Met Thr Lys Gln Ser Ser Ile Lys
  1               5                  10                  15

Asn Asn Leu Met Leu Gly Leu Asp Asn Glu Leu Asp Phe Asp Phe Asp
             20                  25                  30

Phe Asp Glu Asp Glu Asp Leu Asp Gln Pro Gln Met Gly Thr Arg Ala
         35                  40                  45

Asp Lys Ser Leu Gly Leu Leu Ala Lys Arg Phe Ile Arg Met Ile Gln
     50                  55                  60

Tyr Ser Pro Tyr Gly Arg Cys Asp Leu Asn Thr Ala Ala Glu Ala Leu
 65                  70                  75                  80

Asn Val Arg Gln Lys Arg Arg Ile Tyr Asp Ile Thr Asn Val Leu Glu
                 85                  90                  95

Gly Ile Gly Leu Ile Glu Lys Arg Ser Lys Asn Met Ile Gln Trp Lys
```

```
                    100                 105                 110
Gly Gly Asp Phe Met Leu Asn Val Lys Glu Gly Lys Arg Leu Ser Ala
            115                 120                 125

Thr Thr Glu Glu Glu Asp Arg Met Glu Gln Leu Lys Ala Glu Ile Glu
        130                 135                 140

Gln Leu Asn Lys Glu Glu Glu Leu Ile Glu Gln Arg Gln Arg Trp Leu
145                 150                 155                 160

Gln Gln Ser Leu Arg Asn Met Thr Glu Ser Val Glu Asn Asn Lys Leu
                165                 170                 175

Ser Tyr Val Leu Arg Ser Gln Leu Ala Glu Ile Gln Gly Ser Asp Leu
            180                 185                 190

Thr Ile Gly Ile Gln Thr Arg Val Gly Thr Gln Val Arg Leu Ser Asp
        195                 200                 205

Pro Glu Gln Val Glu Ile His Gly Gly Pro Ser Trp Cys Tyr Leu Lys
    210                 215                 220

Asp Pro Ser Gly Pro Leu Arg Ala Ala Ile Val Ser Asn His Glu Leu
225                 230                 235                 240

His Asp Phe Val Gln Arg Glu Arg Ala Lys Arg Pro Gly Glu Glu His
                245                 250                 255

Val Asp Ala Asp Ala Pro Asp Glu Met Met Asp Asp Ser Arg Tyr Arg
            260                 265                 270

Asn Arg Arg Thr Ile Asn Asp Asp Glu Met Phe Gly Phe Glu Gln Lys
        275                 280                 285

Val Pro Ala Met Lys His Leu Glu Pro Pro Ala Ser Asp Asp Tyr
    290                 295                 300

Val Tyr Ser Ser Thr Gly Asp Glu Tyr Arg Gly Asp Ser Ile Val Asp
305                 310                 315                 320

Leu Tyr Gly Asp

<210> SEQ ID NO 10
<211> LENGTH: 1428
<212> TYPE: DNA
<213> ORGANISM: Caenorhabditis elegans

<400> SEQUENCE: 10
gtttgagcca tggaagactc gtacaacgac atggaagacc ccggcttccg ccaattatct    60
gacatggagc ttcaaaaagc gctggaaatg accaaacaga gctcgataaa gaacaatttg   120
atgctcgggc tcgacaatga gcttgacttt gattttgatt ttgacgagga tgaggacctg   180
gatcaaccac aaatgggcac acgagccgat aaatcgttgg gattgttggc gaaacgattt   240
attcgaatga ttcagtactc accgtatgga agatgcgatt gaacactgc cgccgaggcg   300 ctcaatgtcc ggcaaaagcg acgaatctac gatattacga atgttctcga aggaattggt   360
cttattgaga aaagaagcaa gaatatgata cagtggaaag gcggtgattt tatgctaaac   420
gtgaaggaag ggaaacgact atcggccaca acagaagaag aagatcgaat ggaacaatta   480
aaagctgaaa ttgagcaatt aaataaggaa gaagagctca ttgagcaacg tcaaagatgg   540
cttcagcaga gcctccgaaa catgacagaa tccgtggaga caacaagct cagctatgtg   600 ctccgttcac agctcgccga gattcaaggc tcagatctta cgattggaat tcaaacgaga   660
gtcggcacac aagttcggct cagtgatccg gagcaagtcg agatacacgg tggaccatct   720
tggtgttacc tgaaagatcc ctctggaccc ctccgagccg ccatcgtttc caaccatgag   780
ctacatgatt ttgtacagag agaacgagca aaacggcctg gtgaagagca cgttgacgct   840
```

-continued

```
gatgctccag atgaaatgat ggatgattca agatatcgga atcggcggac gatcaatgat    900
gatgaaatgt ttggttttga gcagaaagtc ccagcgatga agcatctgga gccaccaccg    960
gccagcgatg actacgttta ttcgagcacc ggagacgagt atcgaggaga ttctatagtc   1020
gatttgtacg gagattaatt attttaatat tttttttta aatttcgaat tctgcgacca    1080
tttctcattt gacatctatt catttactcc aaattccaaa ttttccccca aaaaaattat   1140
cgatgtttcg gctccaaatg ttattatttt cccatccaca gtgcccacac aattcataat   1200
gtgcctctgg agaaaaccta acgtatttca atttctatcc caaatttta ttttcaaaa    1260
atttctcaga tttttaaatt atttgtcaca ctttttctg tattcaaact gaactttttc    1320
acttggattt gtacgtttt ttttttgttc aattttaatg gattttcact tgaaaacccc    1380
aataaaaacg ggataaatcg acgtttttga ataaaaaaaa aaaaaaaa                1428
```

<210> SEQ ID NO 11
<211> LENGTH: 161
<212> TYPE: PRT
<213> ORGANISM: Caenorhabditis elegans

<400> SEQUENCE: 11

Met Ser Arg Pro Leu Gly Phe Ile Gly Tyr Glu Phe Gly Asp Asp Glu
1               5                   10                  15
Met Phe Val Gln Gln Met Ile Glu Lys Lys Ser Asn Ala Glu Gln Ala
            20                  25                  30
Lys Met Leu Glu Gln Gln Lys Lys Met Leu Glu Cys Thr Glu Thr Met
        35                  40                  45
Pro Glu Glu Ser Glu Pro Val Pro Met Lys Cys Leu Asp Phe Glu Glu
    50                  55                  60
Ala Phe Gln Ser Glu Ser Val Ser Lys Gly Tyr Glu Ser Pro Tyr Lys
65                  70                  75                  80
Asn Ile Ser Phe Leu Lys Glu Asp Ala Val Thr Val Asn Thr Met Ser
                85                  90                  95
His Cys Pro Ala Asp Asp Ile Ala Lys Leu Ile Arg Asn Ile Gln Asn
            100                 105                 110
Ser Val Tyr Thr Leu Gly Ile Glu Glu Ala Arg Gln Cys Arg Arg Gly
        115                 120                 125
Lys Leu Leu Asn Val Leu Lys Pro Thr Gly Ser Ala Ser Pro Arg Tyr
    130                 135                 140
Leu Gln Pro Thr Pro Pro Lys Asn Val Ala Glu Glu Thr Thr Gly Ser
145                 150                 155                 160
Gln

<210> SEQ ID NO 12
<211> LENGTH: 493
<212> TYPE: DNA
<213> ORGANISM: Caenorhabditis elegans

<400> SEQUENCE: 12

```
atgtcgcgtc cgctaggatt tattggatac gaatttggag atgacgaaat gttcgtccaa     60
caaatgatcg aaaagaaatc aaacgcagaa caggcgaaaa tgcttgaaca acagaaaaag    120
atgctcgaat gcaccgaaac aatgccagaa gaaagtgagc cagttccaat gaaatgtctc    180
gattttgaag aagcatttca aagcgaatca gtatcaaaag gttacgaatc gccatacaag    240
aatatttcgt ttctcaagga agatgctgtg actgttaata caatgagcca ctgcccagcc    300
gacgatatcg ccaagctcat ccgaaacatt caaaactcgg tgtacactct tggaatcgaa    360
```

```
gaagctcgcc agtgccgacg tggaaagttg ctcaacgtgc tgaaacccac tggctcggct    420
tctccgagat atttgcagcc aacaccaccg aaaaatgtag cggaagaaac gacaggaagc    480
cagtgaaatt gaa                                                        493
```

<210> SEQ ID NO 13
<211> LENGTH: 438
<212> TYPE: PRT
<213> ORGANISM: Caenorhabditis elegans

<400> SEQUENCE: 13

```
Met Asn Gln Gly Glu Ile Val Tyr Gln Asp Asp Asp Tyr Tyr Asp
 1               5                  10                  15

Glu Ser Glu Ile Tyr Asp Asn Tyr Glu Glu Gly Ala Glu Phe Ile Glu
                 20                  25                  30

Val Asn Gly Gln Leu Val Pro His Asn Pro Asn Leu Gln Ala Gln Gln
             35                  40                  45

Asn Arg Pro Gly Thr Ser Ser Met Ile Gln Gln His Asn Arg Ser Met
 50                  55                  60

Glu Val Asn Gln Gly Leu Val Lys Asp Glu Pro Ile Asp Thr Ser Ser
65                  70                  75                  80

His Arg Val Tyr Val Pro Pro Arg Pro Val Gln Arg Lys Leu Trp
                 85                  90                  95

Lys Leu Phe Gln Pro Gly Pro Ser Thr Pro Gly Ser Ser Gln Tyr Thr
                100                 105                 110

Val Arg Asn Leu Ser Asn Leu Ser Gly Ser Pro Ser Met Tyr Asp Arg
            115                 120                 125

Gln Pro Ala Ser Leu Pro Arg Thr Val Gln Pro Met Gly Leu Glu Met
        130                 135                 140

Gly Asn Ser Glu Gln Arg Lys Val Tyr Ile Asp Met Lys Asp His Val
145                 150                 155                 160

Ser His Ile Arg Leu Lys Thr Lys Lys Val Phe Ala Pro Gly Gln
                165                 170                 175

Arg Lys Pro Cys Asn Cys Thr Lys Ser Gln Cys Leu Lys Leu Tyr Cys
                180                 185                 190

Asp Cys Phe Ala Asn Gly Glu Phe Cys Arg Asp Cys Asn Cys Lys Asp
            195                 200                 205

Cys His Asn Asn Ile Glu Tyr Asp Ser Gln Arg Ser Lys Ala Ile Arg
        210                 215                 220

Gln Ser Leu Glu Arg Asn Pro Asn Ala Phe Lys Pro Lys Ile Gly Ile
225                 230                 235                 240

Ala Arg Gly Gly Ile Thr Asp Ile Glu Arg Leu His Gln Lys Gly Cys
                245                 250                 255

His Cys Lys Lys Ser Gly Cys Leu Lys Asn Tyr Cys Glu Cys Tyr Glu
                260                 265                 270

Ala Lys Val Pro Cys Thr Asp Arg Cys Lys Cys Lys Gly Cys Gln Asn
            275                 280                 285

Thr Glu Thr Tyr Arg Met Thr Arg Tyr Lys Asn Ser Gly Gly Ala Val
        290                 295                 300

Ser Asn Thr Asn Ala Leu Met Ser Leu Thr Asn Ala Ser Ser Thr Ala
305                 310                 315                 320

Thr Pro Asp Ser Gly Pro Gly Ser Val Val Thr Asp Glu His Gly Asp
                325                 330                 335

Asp Tyr Glu Asp Met Leu Leu Ser His Lys Pro Lys Val Glu Met Asp
```

-continued

```
             340              345              350
Pro Arg Arg Phe Pro Trp Tyr Tyr Met Thr Asp Glu Val Val Glu Ala
        355              360              365
Ala Thr Met Cys Met Val Ala Gln Ala Glu Glu Ala Leu Asn Tyr Glu
    370              375              380
Lys Val Gln Thr Glu Asp Glu Lys Leu Ile Asn Met Glu Lys Leu Val
385              390              395              400
Leu Arg Glu Phe Gly Arg Cys Leu Glu Gln Met Ile Thr Asn Thr Thr
                405              410              415
Glu Leu Thr Gln Asp Leu Asp Ala Ala Pro Thr Asp Asp Ile Pro Gly
            420              425              430
Pro Ser Thr Ser Thr Ser
        435
```

<210> SEQ ID NO 14
<211> LENGTH: 1503
<212> TYPE: DNA
<213> ORGANISM: Caenorhabditis elegans

<400> SEQUENCE: 14

| | | | | | |
|---|---|---|---|---|---|
| attttcagtg | ttgacaatga | atcaaggaga | aatcgtttat | caagacgacg | atgattatta | 60 |
| cgacgaatcg | gagatatacg | ataattatga | agaaggtgcc | gaatttatcg | aagttaatgg | 120 |
| acagcttgtg | cctcataatc | caaacttaca | ggcgcagcaa | aatcgtccgg | gaacctcgag | 180 |
| tatgattcaa | cagcataatc | gatcaatgga | agttaatcag | ggattggtca | agacgaacc | 240 |
| aattgataca | tcatcgcatc | gcgtctacgt | cccccctccg | agaccagttc | agcgaaaact | 300 |
| ttggaagctt | tttcagcctg | ggcccagcac | tcccggatcg | tctcagtaca | ctgtgcggaa | 360 |
| tttgtccaat | ttatcgggtt | caccttcaat | gtacgatcga | cagcccgctt | cattacctag | 420 |
| aacagtgcaa | ccaatgggct | tggagatggg | aaattctgaa | cagcgaaaag | tttacatcga | 480 |
| tatgaaagat | cacgttagtc | atattagatt | gaaaactaaa | aaaaaagtat | ttgcacctgg | 540 |
| ccagcggaaa | ccatgcaatt | gcacgaaatc | tcaatgcctc | aagctctact | gtgattgttt | 600 |
| cgccaatgga | gagttctgtc | gtgactgcaa | ttgcaaggat | tgtcacaata | atatagaata | 660 |
| cgacagtcag | cgttcaaaag | ccatccgtca | gtcacttgag | cgaaatccga | acgctttcaa | 720 |
| gccaaaaatt | ggtattgctc | gtggaggtat | taccgacatc | gaacgtcttc | atcagaaagg | 780 |
| atgtcactgt | aaaagagtg | gttgtctgaa | aaactattgt | gagtgttatg | aagcaaaggt | 840 |
| tccgtgtacc | gatcgatgca | agtgcaaagg | atgtcagaat | actgaaacat | acagaatgac | 900 |
| aagatacaag | aactccggtg | gtgccgtgtc | caatacgaat | gccctgatgt | cattgaccaa | 960 |
| cgcttccagc | acagcgactc | cagattctgg | tccgggaagt | gtggtgaccg | atgagcatgg | 1020 |
| agacgactac | gaggatatgc | ttctttcgca | taaaccgaag | gtcgagatgg | atcctagacg | 1080 |
| cttcccgtgg | tactatatga | ccgatgaagt | cgttgaggca | gccactatgt | gcatggttgc | 1140 |
| tcaagctgaa | gaagctttaa | actacgaaaa | agtgcaaacc | gaagacgaaa | aactcatcaa | 1200 |
| tatggagaag | cttgtccttc | gtgaattcgg | ccgctgtctc | gaacaaatga | tcacaaacac | 1260 |
| aactgagctc | acacaagatc | ttgatgccgc | tccaacggat | gacatcccag | gaccatctac | 1320 |
| tagtacttct | taactattcg | cattaaaatt | attatcaatt | ttatcacagt | tgcgcgatct | 1380 |
| tttatgatct | cacctctcac | acattctttg | ccttcctccc | ctcctctcaa | tgcttttaca | 1440 |
| gattcacaag | ttgccttctt | tcaaagttgt | caaataaaaa | atgatcagaa | aaatttgttt | 1500 |
| cat | | | | | | 1503 |

<210> SEQ ID NO 15
<211> LENGTH: 449
<212> TYPE: DNA
<213> ORGANISM: Mus musculus

<400> SEQUENCE: 15

```
gtgctaaaac aattggtgaa ccagacttgc ccaaagttgt taatattaac ttctgtccat      60
ctggtttaag ggtctgattg ccaagtttaa gatcagatgt ctgtgatact ttgtttaaaa     120
taatctgatt ggctgatata gtcacaggag tctgagcacc aagttttga aggccacttg      180
gaaatgctgg tttcactgtg gtattagaat ctgctttaga aactgtggta ttcactgcaa     240
cttggttagt gtggttactg tacactgtga ttggttccgt ggaaatgggc gtggctgtag     300
agtcaccggt agaatttatg ttgacaattt cttccagctc tgtctccatg ggaattgggg     360
atgcacacaat tacagcctca atactatcct catccactaa cgttatagca gtgtccatta     420
tgtcgtctgg aagcaaacta ttcactcgg                                        449
```

<210> SEQ ID NO 16
<211> LENGTH: 3535
<212> TYPE: DNA
<213> ORGANISM: Homo sapiens
<220> FEATURE:
<221> NAME/KEY: misc_feature
<222> LOCATION: (1)...(3535)
<223> OTHER INFORMATION: n = A,T,C or G

<400> SEQUENCE: 16

```
aaactggtcc aagctgaatt ccggggaaaa ggtgaaaatg gcggatcttt cgaaatacaa      60
tcccggcccc tgacatacca gaggcggcgg cgacggcgac gtcgccaacc cggctcccTT     120
ctcggtcccc gggtaccctg gagcgctcca gtttggacaa actgggaaag gaagctgctg     180
gccagagcta tcgtgcacgg gcaaaacaag ccccgccggg gctcgggatt gcccaggacc     240
ttccggagcc cctacctcgg agcccgaggg aggagaaagc ggcagccgct ggagtgcctg     300
atcaactttc tagcgggaga acgatcatgg aggtggtgcc agctgagtg aatagtttgc      360
ttccagagga ataatggac actggtataa ctttagtgga tgatgatagt attgaggctg      420
ttattgtttc atccccaatt cccatggaga cagaactgga agaaattgtc aacataaatt     480
ctactggtga ctctacagcc acgcccattt ccacggaacc aatcacagtg tacagtaacc     540
acactaacca agttgcagtg aataccacaa ttactaaagc agattctaat accacagtga     600
aaccagcttt tccaagtggc cttcaaaaac ttggtgctca gactcctgtg actatatcag     660
ccaatcagat tatttaaac aaagtatcac agacatctga tcttaaactt ggcaatcaga      720
cccttaaacc agatggacag aagttaattt taacaacttt gggcaagtct ggttcaccaa     780
ttgttttagc actacccat agccaactac cccaggctca gaaagttaca actcaggccc      840
agtcaggaga tgctaagtta ccaccgcagc aaattaaagt agttaccatt ggagggaggc     900
cagaggtgaa acctgtcatt ggtgtctcag cattgacccc aggaagtcaa ctgattaata     960
ctacaactca gccctctgtg ttacagaccc aacagttaaa acagtacag attgctaaga    1020
agcctcgaac gccaacctct ggtccagtaa tcacgaagct gatctttgca aaaccaatta    1080
atagtaaagc agttacagga cagacaactc aagtttcacc accagtcatt gcaggtaggg    1140
ttcttttcaca gtctactccc ggaactccat caaagaccat aacaatatct gaaagtggtg    1200
ttattggatc aactttaaat tctacaacac agacaccaaa taaatagcc atctcacctt     1260
```

-continued

```
tgaaatcgcc aaataaggca gtgaaatcaa ctgtgcagac catcactgtt ggaggagtga   1320
gcacatcaca gtttaagaca attattcctc tggcaactgc tcccaatgtc cagcagattc   1380
aagtgcctgg aagcaagttt cattatgtcc gacttgttac tgccacatca gccagtagct   1440
caacccagcc agttagtcag aatcccagta caaacactca gccttttcag caagcaaagc   1500
cagtggttgt aatacaacc ccagtgcgga tgtcagttcc aattgtctca gctcaggctg   1560
tcaaacaagt tgttccaaaa ccaatcaatc caacttcaca aatagtaact actagccagc   1620
cacagcaacg gcttatcatg cctgccacac cactgccaca gatccagccc aacctcacta   1680
acctgccacc aggcactgtc ctggcaccag ctccgggaac agggaatgtg ggttatgcag   1740
tgcttccagc tcagtatgtt actcagctac agcagtcttc atatgtatca atagcaagca   1800
actctacctt tactgaaaca tctggtatcc agacccaggc acggcttcca ttcaatggca   1860
taatcccatc agagtcggcc agtcggcccc gaaagccctg taattgtaca aaatcactgt   1920
gtttgaaatt gtattgtgat tgctttgcaa atggtgaatt ttgcaacaac tgcaattgta   1980
ctaattgtta caacaatttg gaacatgaaa atgaaaggca aaaagcaata aaggcatgcc   2040
ttgacagaaa tccagaagcc tttaagccta agatagggaa aggaaaggag ggagaatctg   2100
atcgacgtca tagcaaaggg tgtaattgca aacgatcagg atgtcttaaa aactactgtg   2160
aatgctatga ggcaaaaata atgtgttcct caatatgcaa atgtattggc tgtaagaatt   2220
ttgaagaaag cccggaaagg aagacattga tgcatttggc agatgcagct gaagtaaggg   2280
tacagcaaca aacagcagcc aagacgaagt tatcctctca aatttcagac ttgcttacta   2340
ggccaacacc agctttaaat agtggaggcg gaaaattgcc atttacattt gtaactaagg   2400
aantanctga agccacntgt aattgccncc ttgcccaggc agagcaggca gacaagaagg   2460
gaaaatcaaa ggcagcagcg gaacggatga tacttgagga atncggacna tgtttgatga   2520
ntgtcatcaa ctctgcagga aaggcaaaaa ntgacccttg tgcccatgaa ttgctaactc   2580
ttgcacaaaa gactgataaa tggaactgta cagaaaattt aaggtgcagg gacacttgat   2640
tttctggaag aaaaacaatt actgtatttt aattcagtcc ttgttttaaa agacctgaaa   2700
ttataatact gaaggagaag aaattttaaa tgaggaaatt agtacatttt aaatcttagt   2760
taaatctgct tatgccccctt ctaaattgaa ttttctnta ttatatagat ttttaatttt   2820
gcttgggttt cttaagaatt agatgttctc tttctgatac ctttgacaaa aatgtttat   2880 aaattcatat aatttataat gtatggtgtt gtatgacttt gttaatagaa aagccaaagc   2940
agcagtggtt agcacccatt ctttgggact tgatctagaa tatctgcaga cagaatgtta   3000
cataaacaaa ttcttatgaa acacattcaa atgacatttt gtatttagaa aaggactatc   3060
ttttaaagaa aaagcagcct tttagggccg attctggaat aatatcctgt tgtcactttg   3120
ggaatgtcag aaggggaaac aatccccagg cacactaaaa attttttaaa gttatttaaa   3180
aaaacatata aatatttaaa ggacagtaaa tctcagagga tgggcaatgt gtttctataa   3240
taaggaaagg ctaacagatg ctctgggctg tctccatttt ctttcaaaga ggtggtatgt   3300
atttgaagta ataaattgtc aaagtgatta ctgggtacta ttaaaatgat aggtggatat   3360
aaatggaagt aaacattatg tagtgataat atagaacctc acatagtaat caagtataaa   3420
atttggcatg ggtggagaaa caaagnatcg ggaagctgcc aaagatgaat ttagagaagt   3480
tttcatctat acaatcaatt atttttacag acttttttc cggaattctt ttgct         3535
```

<210> SEQ ID NO 17
<211> LENGTH: 30

```
-continued

<212> TYPE: PRT
<213> ORGANISM: Caenorhabditis elegans
<220> FEATURE:
<221> NAME/KEY: VARIANT
<222> LOCATION: (1)...(30)
<223> OTHER INFORMATION: Xaa = Any Amino Acid other than Cys

<400> SEQUENCE: 17

Cys Xaa Cys Xaa Xaa Xaa Xaa Cys Xaa Xaa Xaa Xaa Cys Xaa Cys Xaa
 1               5                  10                  15

Xaa Xaa Xaa Xaa Xaa Cys Xaa Xaa Cys Xaa Cys Xaa Xaa Cys
             20                  25                  30

<210> SEQ ID NO 18
<211> LENGTH: 31
<212> TYPE: PRT
<213> ORGANISM: Caenorhabditis elegans
<220> FEATURE:
<221> NAME/KEY: VARIANT
<222> LOCATION: (1)...(31)
<223> OTHER INFORMATION: Xaa = Any Amino Acid other than Cys

<400> SEQUENCE: 18

Cys Xaa Cys Xaa Xaa Xaa Xaa Cys Xaa Xaa Xaa Xaa Cys Xaa Cys Xaa
 1               5                  10                  15

Xaa Xaa Xaa Xaa Xaa Cys Xaa Xaa Xaa Cys Xaa Cys Xaa Xaa Cys
             20                  25                  30
```